(12) United States Patent
Yang et al.

(10) Patent No.: US 12,605,740 B2
(45) Date of Patent: Apr. 21, 2026

(54) SEMICONDUCTOR DEVICE WITH TRANSDUCER AND METHOD FOR FORMING THE SAME

(71) Applicant: TAIWAN SEMICONDUCTOR MANUFACTURING COMPANY LTD., Hsinchu (TW)

(72) Inventors: Ming-Hsien Yang, Taichung City (TW); Chun-Hao Chou, Tainan City (TW); Kuo-Cheng Lee, Tainan City (TW); Sheng Kai Yeh, Taichung City (TW)

(73) Assignee: TAIWAN SEMICONDUCTOR MANUFACTURING COMPANY LTD., Hsinchu (TW)

( * ) Notice: Subject to any disclaimer, the term of this patent is extended or adjusted under 35 U.S.C. 154(b) by 784 days.

(21) Appl. No.: 17/819,044

(22) Filed: Aug. 11, 2022

(65) Prior Publication Data

US 2024/0050987 A1     Feb. 15, 2024

(51) Int. Cl.
| | |
|---|---|
| B06B 1/02 | (2006.01) |
| B06B 1/06 | (2006.01) |
| *A61B 5/00* | (2006.01) |

(52) U.S. Cl.
CPC .......... B06B 1/0292 (2013.01); B06B 1/0666 (2013.01); *A61B 5/0095* (2013.01); *B06B 2201/76* (2013.01)

(58) Field of Classification Search
None
See application file for complete search history.

(56) References Cited

U.S. PATENT DOCUMENTS

| | | | | |
|---|---|---|---|---|
| 9,796,582 B1 * | 10/2017 | Cheng | .............. | H01L 23/53295 |
| 2020/0413202 A1 * | 12/2020 | Kusano | .................. | H04R 31/00 |
| 2021/0165985 A1 * | 6/2021 | Grip | ................... | G06V 40/1306 |
| 2021/0404994 A1 * | 12/2021 | Pushparaj | ............ | B06B 1/0292 |
| 2022/0362804 A1 * | 11/2022 | Chiu | .................... | B06B 1/0292 |
| 2023/0125688 A1 * | 4/2023 | Wang | ................. | G01S 7/52079 |
| | | | | 73/596 |

* cited by examiner

*Primary Examiner* — Michelle Mandala
(74) *Attorney, Agent, or Firm* — WPAT LAW; Anthony King

(57) ABSTRACT

A semiconductor device and a method are provided. The semiconductor device includes a first semiconductor component, a bonding layer and a second semiconductor component. The first semiconductor component includes a first transistor formed on a substrate and a second transistor formed on the substrate and separated from the first transistor. The bonding layer is provided on the first semiconductor component. The second semiconductor component is provided on the bonding layer and includes an acoustic transducer. The acoustic transducer is controlled by the first transistor and the second transistor to execute a photoacoustic sensing. The acoustic transducer comprises a space gap and a least a portion of the space gap is surrounded by the bonding layer.

20 Claims, 20 Drawing Sheets

SEMICONDUCTOR DEVICE WITH TRANSDUCER AND METHOD FOR FORMING THE SAME

BACKGROUND

The present disclosure relates, in general, to semiconductor devices and methods for manufacturing the same. Specifically, the present disclosure relates to semiconductor devices and methods for manufacturing semiconductor products for image detecting.

Acoustic-based imaging and light-based imaging have been widely used for various applications, such as security or healthcare. However, the imaging might be limited in differentiating between soft tissues structures. Also, the accuracy may be affected by the scattering of light.

BRIEF DESCRIPTION OF THE DRAWINGS

Aspects of the embodiments of the present disclosure are best understood from the following detailed description when read with the accompanying figures. It should be noted that, in accordance with standard practice in the industry, various structures are not drawn to scale. In fact, the dimensions of the various structures can be arbitrarily increased or reduced for clarity of discussion.

FIG. 8A is schematic views of a semiconductor system, in accordance with some embodiments of the present disclosure.

FIG. 8B is schematic views of a light emitting device, in accordance with some embodiments of the present disclosure.

FIG. 8C is schematic views of a semiconductor system, in accordance with some embodiments of the present disclosure.

FIG. 9A is schematic views of a semiconductor system, in accordance with some embodiments of the present disclosure.

FIG. 9B is schematic views of a light emitting device, in accordance with some embodiments of the present disclosure.

FIG. 9C is schematic views of a semiconductor system, in accordance with some embodiments of the present disclosure.

DETAILED DESCRIPTION

Figure 1B:
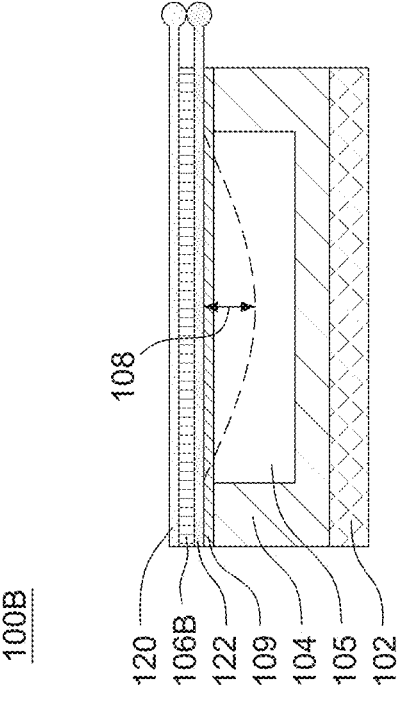
FIG. 1B is a schematic view of another acoustic transducer, in accordance with some embodiments of the present disclosure.

The following disclosure provides many different embodiments, or examples, for implementing different features of the provided subject matter. Specific examples of elements and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features can be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "over," "upper," "on" and the like, can be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus can be otherwise oriented (rotated 90 degrees or at other orientations) and the spatially relative descriptors used herein may likewise be interpreted accordingly.

As used herein, although terms such as "first," "second" and "third" describe various elements, components, regions, layers and/or sections, these elements, components, regions, layers and/or sections should not be limited by these terms. These terms may only be used to distinguish one element, component, region, layer or section from another. Terms such as "first," "second" and "third" when used herein do not imply a sequence or order unless clearly indicated by the context.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in the respective testing measurements. Also, as used herein, the terms "substantially," "approximately" and "about" generally mean within a value or range that can be contemplated by people having ordinary skill in the art. Alternatively, the terms "substantially," "approximately" and "about" mean within an acceptable standard error of the mean when considered by one of ordinary skill in the art. People having ordinary skill in the art can understand that the acceptable standard error may vary according to different technologies. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the terms "substantially," "approximately" or "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques. Ranges can be expressed herein as from one endpoint to another endpoint or between two endpoints. All ranges disclosed herein are inclusive of the endpoints, unless specified otherwise.

Figure 1A:
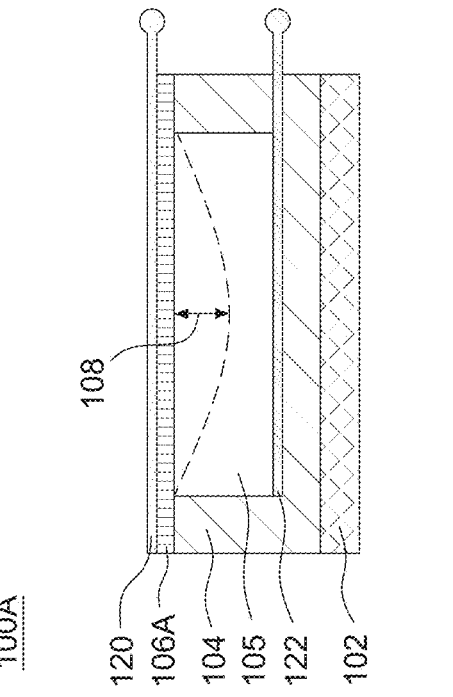
FIG. 1A is a schematic view of an acoustic transducer, in accordance with some embodiments of the present disclosure.

FIG. 1A is a schematic view of an acoustic transducer 100A, in accordance with some embodiments of the present disclosure. The acoustic transducer 100A may include a substrate 102, an insulating layer 104, a space gap 105, a membrane 106A, and two electrodes 120 and 122. In some embodiments, the acoustic transducer 100A may be a micro-machined acoustic transducer. In some embodiments, the acoustic transducer 100A may be a capacitive micro-machined acoustic transducer (CMUT).

The substrate 102 may include a semiconductor substrate. In some embodiments, the substrate 102 may include, for example, silicon (Si), monocrystalline silicon, polysilicon, amorphous silicon, germanium (Ge), silicon germanium (SiGe), silicon carbide (SiC), silicon germanium carbide (SiGeC), gallium (Ga), gallium arsenide (GaAs), indium (In), indium arsenide (InAs), indium phosphide (InP) or other IV-IV, III-V or II-VI semiconductor materials. In some other embodiments, the substrate 102 may include a layered semiconductor such as silicon/silicon germanium, silicon-on-insulator, or silicon germanium-on-insulator.

The insulating layer 104 may include a gate oxide layer. In some embodiments, the insulating layer 104 may include, for example, silicon oxide ($SiO_2$), silicon nitride ($Si_3N_4$), silicon oxynitride ($N_2OSi_2$), silicon nitride oxide ($N_2OSi_2$), a high-k material or combinations thereof. Examples of the high-k material include a dielectric material having a dielectric constant higher than that of silicon dioxide ($SiO_2$), or a dielectric material having a dielectric constant higher than about 3.9. In some embodiments, the insulating layer 104 may include at least one metallic element, such as hafnium oxide ($HfO_2$), silicon doped hafnium oxide (HSO), lanthanum oxide ($La_2O_3$), lanthanum aluminum oxide ($LaAlO_3$), zirconium oxide ($ZrO_2$), zirconium orthosilicate ($ZrSiO_4$), aluminum oxide ($Al_2O_3$) or combinations thereof.

The membrane 106A may include, for example, silicon oxide (SiO2), silicon nitride ($Si_3N_4$), silicon oxynitride ($N_2OSi_2$), silicon nitride oxide ($N_2OSi_2$). In some embodiments, the membrane 106A may include at least one metallic element, such as hafnium oxide ($HfO_2$), silicon doped hafnium oxide (HSO), lanthanum oxide ($La_2O_3$), lanthanum aluminum oxide ($LaAlO_3$), zirconium oxide ($ZrO_2$), zirconium orthosilicate ($ZrSiO_4$), aluminum oxide ($Al_2O_3$) or combinations thereof.

In some embodiments, the membrane 106A may include a shape of circle, oval, triangle, rectangle or hexagon. More specifically, the membrane displacement is highest for a circular shape under same uniform pressure and area of vibration. Moreover as the distance between the elemental membranes increases the displacement decreases for the membrane 106A with circular and hexagonal shapes, while the reverse behavior is observed for the membrane 106A with rectangular and triangle shapes.

The electrodes 120 and 122 may is, or includes, a conductive material such as a metal or metal alloy. Examples include gold (Au), silver (Ag), aluminum (Al), copper (Cu), chromium (Cr), tin (Sn), nickel (Ni) another metal, or a mixture, an alloy, or other combination of two of more thereof. In some embodiments, the membrane 106A may be physically separated from the electrode 122. In some embodiments, the membrane 106A may be spaced apart from the electrode 122 by the space gap 105.

In some embodiments, the space gap 105 may be formed within the insulating layer 104. The space gap 105 may be surrounded by the membrane 106A, the insulating layer 104 and the electrode 122. The space gap 105 may be defined as a space encircled by the membrane 106A, the insulating layer 104 and the electrode 122. The space gap 105 may be used to allow vibrations of the membrane 106A. For example, as shown in FIG. 1A, the membrane 106A could be deflected toward the electrode 122 with a distance 108.

In some embodiments, the acoustic transducer 100A may be used for scanning images. For example, the acoustic transducer 100A could be used to detect or obtain an image of vein and tissue of human. In some embodiments, the acoustic transducer 100A may be powered by a battery or a voltage source. In some embodiments, the vibrating frequency of the membrane 106A could be calculated or analyzed. In some embodiments, the acoustic transducer 100A may have high bandwidth and high resolution. In some embodiments, the acoustic transducer 100A may be suitable for high frequency applications. The acoustic transducer 100A may be applicable for scanning images in deep level of vein and tissue.

FIG. 1B is a schematic view of an acoustic transducer 100B, in accordance with some embodiments of the present disclosure. In some embodiments, the acoustic transducer 100B may be a micro-machined acoustic transducer. In some embodiments, the acoustic transducer 100B may be a piezoelectric micro-machined acoustic transducer (PMUT).

The acoustic transducer 100B of FIG. 1B is similar to the acoustic transducer 100A of FIG. 1A, except for the differences described as follows.

The acoustic transducer 100B may include the membrane 106B and a dielectric layer 109. The membrane 106B may be arranged between the electrodes 120 and 122. The membrane 106B may be in direct contact with the electrodes 120 and 122. In some embodiments, the dielectric layer 109 may be formed between the electrode 122 and the insulating layer 104. The dielectric layer 109 may be in direct contact with the electrode 122 and the insulating layer 104.

The membrane 106B may include, for example, silicon oxide ($SiO_2$), silicon nitride ($Si_3N_4$), silicon oxynitride ($N_2OSi_2$), silicon nitride oxide ($N_2OSi_2$). In some embodiments, the membrane 106B may include at least one metallic element, such as hafnium oxide ($HfO_2$), silicon doped hafnium oxide (HSO), lanthanum oxide ($La_2O_3$), lanthanum aluminum oxide ($LaAlO_3$), zirconium oxide ($ZrO_2$), zirconium ortho silicate ($ZrSiO_4$), aluminum oxide ($Al_2O_3$) or combinations thereof. In some embodiments, the membrane 106B may include a piezoelectric layer. In some embodiments, the membrane 106B may directly contact the electrodes 120 and 122.

In some embodiments, the membrane 106B may include a shape of circle, oval, triangle, rectangle or hexagon. More specifically, the membrane displacement is highest for a circular shape under same uniform pressure and area of vibration. Moreover, as the distance between the elemental membranes increases the displacement decreases for the membrane 106B with circular and hexagonal shapes, while the reverse behavior is observed for the membrane 106B with rectangular and triangle shapes.

In some embodiments, the space gap 105 may be formed within the insulating layer 104. The space gap 105 may be surrounded by the dielectric layer 109 and the insulating layer 104. The space gap 105 may be defined as a space encircled by the dielectric layer 109 and the insulating layer 104. The space gap 105 may be used to allow vibrations of the membrane 106B. For example, as shown in FIG. 1B, the membrane 106B could be deflected toward the electrode 122 with a distance 108.

In some embodiments, the acoustic transducer 100B may be used for scanning images. For example, the acoustic transducer 100B could be used to detect or obtain an image of vein and tissue of human. In some embodiments, the acoustic transducer 100B may be avoid of a battery or a voltage source. In some embodiments, the vibrating frequency of the membrane 106B could be calculated or analyzed. In some embodiments, the acoustic transducer 100B may have lower bandwidth than that of the acoustic transducer 100A. In some embodiments, the acoustic transducer 100B may consume less power than that of the acoustic transducer 100A. In some embodiments, the acoustic transducer 100B may be suitable for low frequency applications. The acoustic transducer 100B may be applicable for scanning images in shallow level of vein and tissue.

Figure 2A:
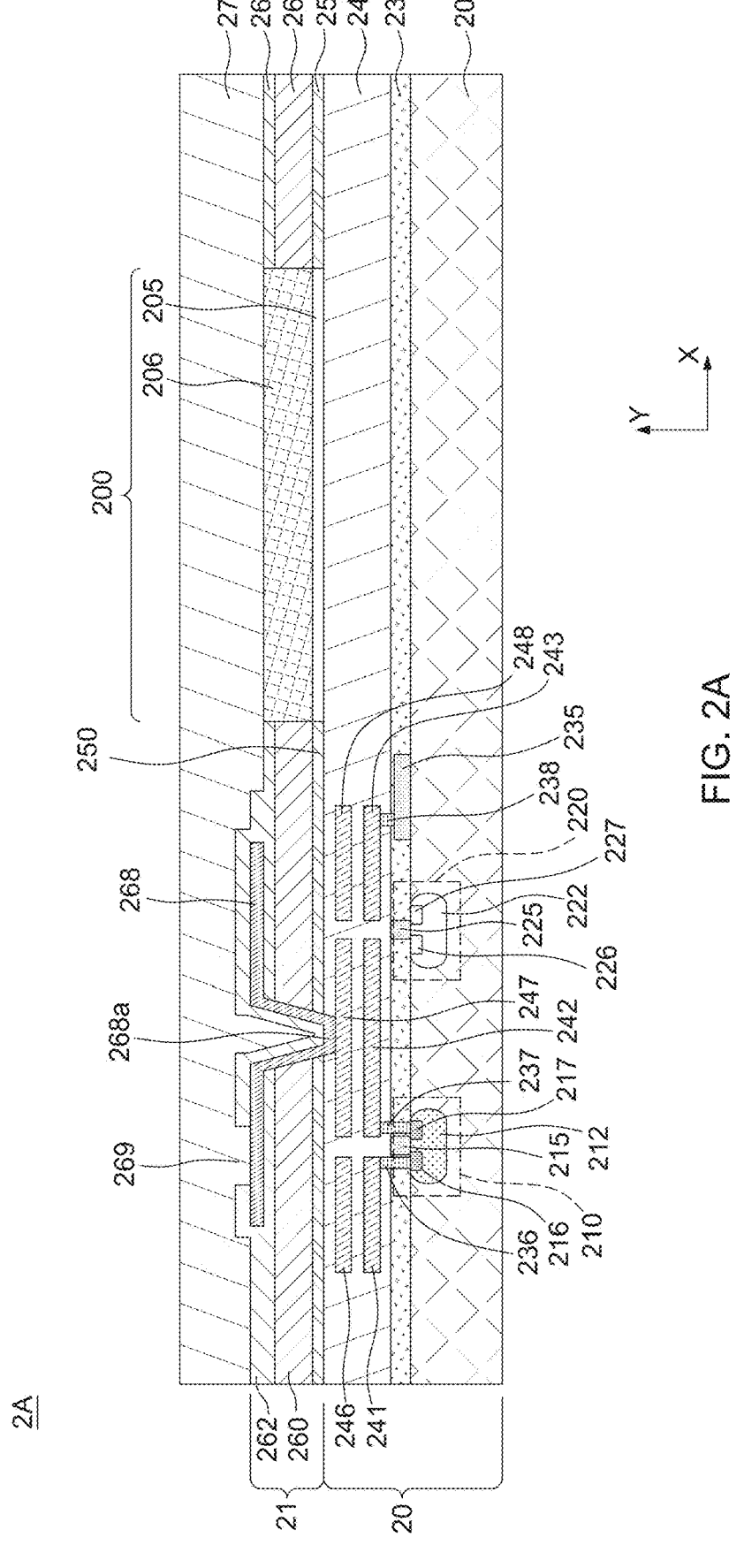
FIG. 2A is a schematic view of a semiconductor device, in accordance with some embodiments of the present disclosure.

FIG. 2A is a schematic view of a semiconductor device 2A, in accordance with some embodiments of the present disclosure. The semiconductor device 2A may include a semiconductor component 20, the semiconductor component 21 and a bonding layer 250. The bonding layer 250 may be formed between the semiconductor component 20 and the semiconductor component 21. The semiconductor component 21 may be attached to the semiconductor component 20 through the bonding layer 250.

In some embodiments, the semiconductor component 20 may include a substrate 202, two transistors 210 and 220, two insulating layers 230 and 240, a plurality of metal structures 241 to 248, and a plurality of connecting structures 236 to 238.

The substrate 202 may include a semiconductor substrate. In some embodiments, the substrate 202 may include, for example, silicon (Si), monocrystalline silicon, polysilicon, amorphous silicon, germanium (Ge), silicon germanium (SiGe), silicon carbide (SiC), silicon germanium carbide (SiGeC), gallium (Ga), gallium arsenide (GaAs), indium (In), indium arsenide (InAs), indium phosphide (InP) or other IV-IV, III-V or II-VI semiconductor materials. In some other embodiments, the substrate 202 may include a layered semiconductor such as silicon/silicon germanium, silicon-on-insulator, or silicon germanium-on-insulator.

The insulating layers 230 and 240 may include a gate oxide layer. In some embodiments, the insulating layers 230 and 240 may include, for example, silicon oxide ($SiO_2$), silicon nitride ($Si_3N_4$), silicon oxynitride ($N_2OSi_2$), silicon nitride oxide ($N_2OSi_2$), a high-k material or combinations thereof. Examples of the high-k material include a dielectric material having a dielectric constant higher than that of silicon dioxide ($SiO_2$), or a dielectric material having a dielectric constant higher than about 3.9. In some embodiments, the insulating layers 230 and 240 may include at least one metallic element, such as hafnium oxide ($HfO_2$), silicon doped hafnium oxide (HSO), lanthanum oxide ($La_2O_3$), lanthanum aluminum oxide ($LaAlO_3$), zirconium oxide ($ZrO_2$), zirconium orthosilicate ($ZrSiO_4$), aluminum oxide ($Al_2O_3$) or combinations thereof.

The insulating layer 230 may be formed on the substrate 202. The insulating layer 240 may be formed on the insulating layer 230. The material of the insulating layer 240 may be substantially the same as that of the insulating layer 230. The material of the insulating layer 240 may be different from that of the insulating layer 230. The thickness of the insulating layer 240 may be greater than that of the insulating layer 230. The thickness of the insulating layer 240 may be substantially the same as that of the insulating layer 230.

The transistor 210 may include an active region 212, a gate structure 215, a drain structure 216 and a source structure 217. The source/drain structure(s) may refer to a source or a drain, individually or collectively dependent upon the context. The drain structure 216 and the source structure 217 may be embedded within or surrounded by the active region 212. The drain structure 216 and the source structure 217 may be coplanar with the active region 212. The active region 212, the drain structure 216 and the source structure 217 may be embedded within or surrounded by the substrate 202. The gate structure 215 may be formed on the active region 212. The gate structure 215 may be surrounded by the insulating layer 230.

The transistor 220 may include an active region 222, a gate structure 225, a drain structure 226 and a source structure 227. The source/drain structure(s) may refer to a source or a drain, individually or collectively dependent upon the context. The drain structure 226 and the source structure 227 may be embedded within or surrounded by the active region 222. The drain structure 226 and the source structure 227 may be coplanar with the active region 222. The active region 222, the drain structure 226 and the source structure 227 may be embedded within or surrounded by the substrate 202. The gate structure 225 may be formed on the active region 222. The gate structure 225 may be surrounded by the insulating layer 230. The conductive structure 235 may be surrounded by the insulating layer 230.

In some embodiments, the transistor 210 may be separated from the transistor 220. In some embodiments, the transistor 210 may be NMOS transistor, and the transistor 220 may be PMOS transistor. In some embodiments, the transistor 210 may be PMOS transistor, and the transistor 220 may be NMOS transistor.

The active regions 212 and 222 may be doped with an N-type dopant such as phosphorus (P), arsenic (As), or antimony (Sb). In some other embodiments, the active regions 212 and 222 may be doped with a P-type dopant such as boron (B) or indium (In). In some embodiments, the substrate 202 may be or include an unimplanted area. In some embodiments, the active regions 212 and 222 may have a higher doping concentration than the substrate 202.

The insulating layer 230 may be formed on the substrate 202. The insulating layer 240 may be formed on the insulating layer 230. The metal structures 241, 242, 243, 246, 247, and 248 may be embedded within the insulating layer 240. The metal structures 241, 242, 243, 246, 247, and 248 may extend along X direction. Each of the metal structures 241, 242, 243, 246, 247, and 248 may be spaced apart from each other. The metal structures 241, 242 and 243 may be coplanar. The metal structures 246, 247 and 248 may be coplanar. The metal structures 246, 247 and 248 may be formed above the metal structures 241, 242 and 243.

Moreover, the lengths of the metal structures 242 and 247 could be greater than those of the metal structures 241, 243, 246 and 248. Each of the metal structures 241, 242, 243, 246, 247, and 248 may have substantially the same height. In some embodiments, the metal structure 241, 242, 243 and 246 may be inter metal structures. In some embodiments, the metal structure 247 and 248 may be top metal structures.

In some embodiments, the drain structure 216 may be electrically connected to the metal structure 241 through the connecting structure 236. The connecting structure 236 could be surrounded by the insulating layer 230 and a portion of the insulating layer 240. In some embodiments, the source structure 217 may be electrically connected to the metal structure 242 through the connecting structure 237. The connecting structure 237 could be surrounded by the insulating layer 230 and a portion of the insulating layer 240. In some embodiments, the conductive structure 235 may be electrically connected to the metal structure 243 through the connecting structure 238. The connecting structure 238 could be surrounded by the insulating layer 230 and a portion of the insulating layer 240.

The bonding layer 250 may be used to combine the semiconductor components 20 and 21. Bonding techniques, which may refer to bonding that involves two or more materials, can be used to form a semiconductor device 2A. In some embodiments, hybrid bonding technique can be used to form a semiconductor device 2A. The semiconductor device 2A can be formed by heat and compression. Hybrid bonding can refer to bonding that involves two or more materials (e.g. metal-to-metal bonding and dielectric-to-dielectric bonding). The semiconductor component 21 can be bonded to the semiconductor component 20 through the bonding layer 250 along Y direction, which is vertical to X direction.

In some embodiments, the semiconductor component 21 may include an acoustic transducer 200, a passivation layer 260, a passivation layer 262 and a via structure 268. The passivation layer 260 may be formed on the bonding layer 250. The passivation layer 262 may be formed on the passivation layer 260.

In some embodiments, the passivation layers 260 and 262 may include silicon oxide, silicon nitride, gallium oxide, aluminum oxide, scandium oxide, zirconium oxide, lanthanum oxide or hafnium oxide. The material of the passivation layer 260 may be substantially the same as that of the passivation layer 262. The material of the passivation layer 260 may be different from that of the passivation layer 262. The thickness of the passivation layer 260 may be greater than that of the passivation layer 262. The thickness of the passivation layer 260 may be substantially the same as that of the passivation layer 262.

In some embodiments, the via structure 268 may penetrate the passivation layer 260. The bottom portion 268a of the via structure 268 may extend into the passivation layer 260. In some embodiments, the portion bottom 268a may include or become a through silicon via (TSV). The via structure 268 may be surrounded by the insulating layer 240, the bonding layer 250, and the passivation layers 260 and 262. In some embodiments, the passivation layer 262 may cover all of the via structure 268. In some embodiments, the passivation layer 262 may cover most portions of the via structure 268. In some embodiments, a portion of the via structure 268 could be uncovered by the passivation layer 262. In some embodiments, a portion of the via structure 268 may be exposed from the passivation layer 262 to form the contact 269. The contact 269 may be configured to receive a power signal, a voltage signal or a control signal.

In some embodiments, the acoustic transducer 200 may include a membrane 206 and a space gap 205. The membrane 206 and the space gap 205 may extend along X direction. The acoustic transducer 200 may be formed on the passivation layer 240. The acoustic transducer 200 may be similar to the acoustic transducer 100A in FIG. 1A or the acoustic transducer 100B in FIG. 1B. Therefore, some detailed descriptions may refer to the corresponding paragraphs here and are not repeated hereinafter for conciseness and simplicity.

In some embodiments, the acoustic transducer 200 may be driven or controller by the transistors 210 and 220. The acoustic transducer 200 may be configured to execute a photoacoustic sensing. The acoustic transducer 200 may be configured to perform a biomedical sensing, for example, on the tissue or the vein.

In some embodiments, the entire space gap 205 may be surrounded by the bonding layer 250. In some embodiments, a portion of the space gap 250 may be surrounded by the bonding layer 250. In some embodiments, lateral surfaces of the space gap 250 may directly contact the bonding layer 250. In some embodiments, a bottom surfaces of the space gap 250 may directly contact the insulating layer 240. The thickness of the space gap 205 may be substantially the same as that of the bonding layer 250. The thickness of the space gap 205 may be smaller than that of the bonding layer 250. The thickness of the space gap 205 may be greater than that of the bonding layer 250.

In some embodiments, the membrane 206 may be surrounded by the passivation layer 260. In some embodiments, the membrane 206 may be surrounded by the passivation layers 260 and 262. In some embodiments, lateral surfaces of the membrane 206 may directly contact the passivation layer 260. In some embodiments, a bottom surfaces of the membrane 206 may directly contact the space gap 205. The thickness of the membrane 206 may be substantially the same as that of the passivation layer 260. The thickness of the membrane 206 may be smaller than that of the passivation layer 260. The thickness of the membrane 206 may be greater than that of the passivation layer 260.

In some embodiments, the acoustic transducer 200 may overlap at least one of the transistors 210, 220, and the metal structures 241 to 248 in the X direction. In some embodiments, the acoustic transducer 200 may overlap at least one of the transistors 210, 220, and the metal structures 241 to 248 in the Y direction. In some embodiments, the acoustic transducer 200 may not overlap at least one of the transistors 210, 220, and the metal structures 241 to 248 in the X direction. In some embodiments, the acoustic transducer 200 may not overlap the transistors 210, 220, and the metal structures 241 to 248 in the Y direction.

In some embodiments, the semiconductor device 2A may include a matching material 270. The matching material 270 may be formed on the passivation layer 260. The matching material 270 may cover the passivation layer 260 and the acoustic transducer 200. The matching material 270 may include silicone based material, porous dielectric material, or soft porous silicon rubbers. The matching material 270 may include medical ultrasound gel (a synthetic polyacrylic acid polymer as a thickening agent), methylparaben and propylparaben (as a preservative), aloe vera gel (as an anti-inflammatory agent), glycerine (as a skin-conditioning agent), disodium EDTA (as a chelating agent), distilled water (as a vehicle), or TEA (as a neutralizing agent).

In some embodiments, the matching material 270 may be used to reduce sound wave transmission resistance due to its low impedance. In some embodiments, an impedance of the matching material 270 could be smaller than that of the space gap 205. In some embodiments, an impedance of the matching material 270 could be smaller than that of the insulating layer 240. The impedance of the matching material 270 could be smaller than that of the insulating layer 230. The impedance of the matching material 270 could be smaller than that of the passivation layer 260. The impedance of the matching material 270 could be smaller than that of the passivation layer 262.

Figure 2B:
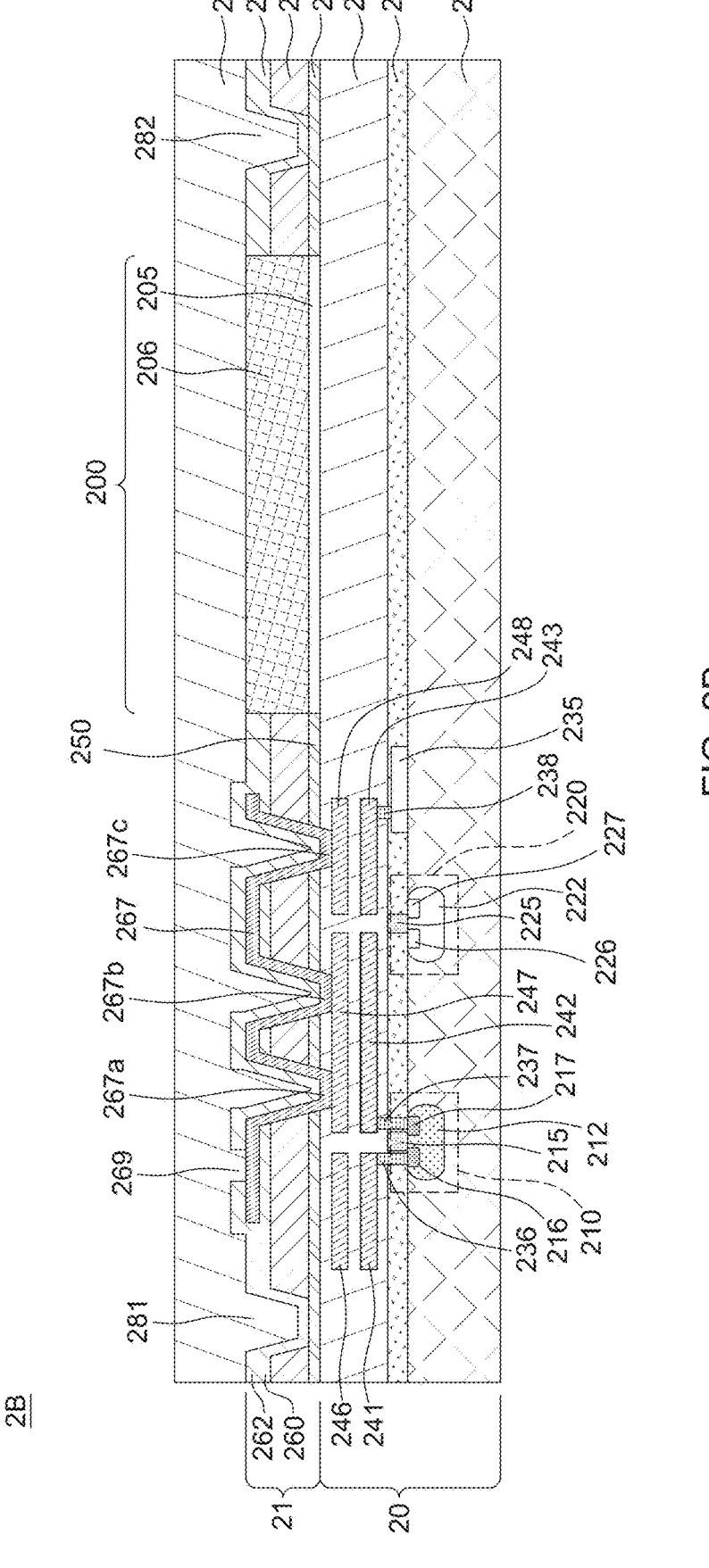
FIG. 2B is a schematic view of another semiconductor device, in accordance with some embodiments of the present disclosure.

FIG. 2B is a schematic view of the semiconductor device 2B, in accordance with some embodiments of the present disclosure. The semiconductor device 2B of FIG. 2B may be similar to the semiconductor device 2A of FIG. 2A, except for the differences described as follows.

The semiconductor device 2B may include a via structure 267, an isolating structure 281 and an isolating structure 282. In some embodiments, the via structure 267 may include three bottom portions 267a, 267b and 267c extending into the insulating layer 240. The bottom portions 267a, 267b and 267c could be spaced apart from each other. The bottom portion 267a may directly contact a top surface of the metal structure 247. The bottom portion 267b may directly contact a top surface of the metal structure 247. The bottom portion 267c may directly contact a top surface of the metal structure 248.

The isolating structures 281 and 282 may be included by the semiconductor component 21. The isolating structures 281 and 282 may be covered by the matching material 270. The isolating structures 281 and 282 may include a deep trench isolation (DTI). The isolating structures 281 and 282 may be used to electrically isolate the semiconductor device 2B from another semiconductor device.

Figure 2C:
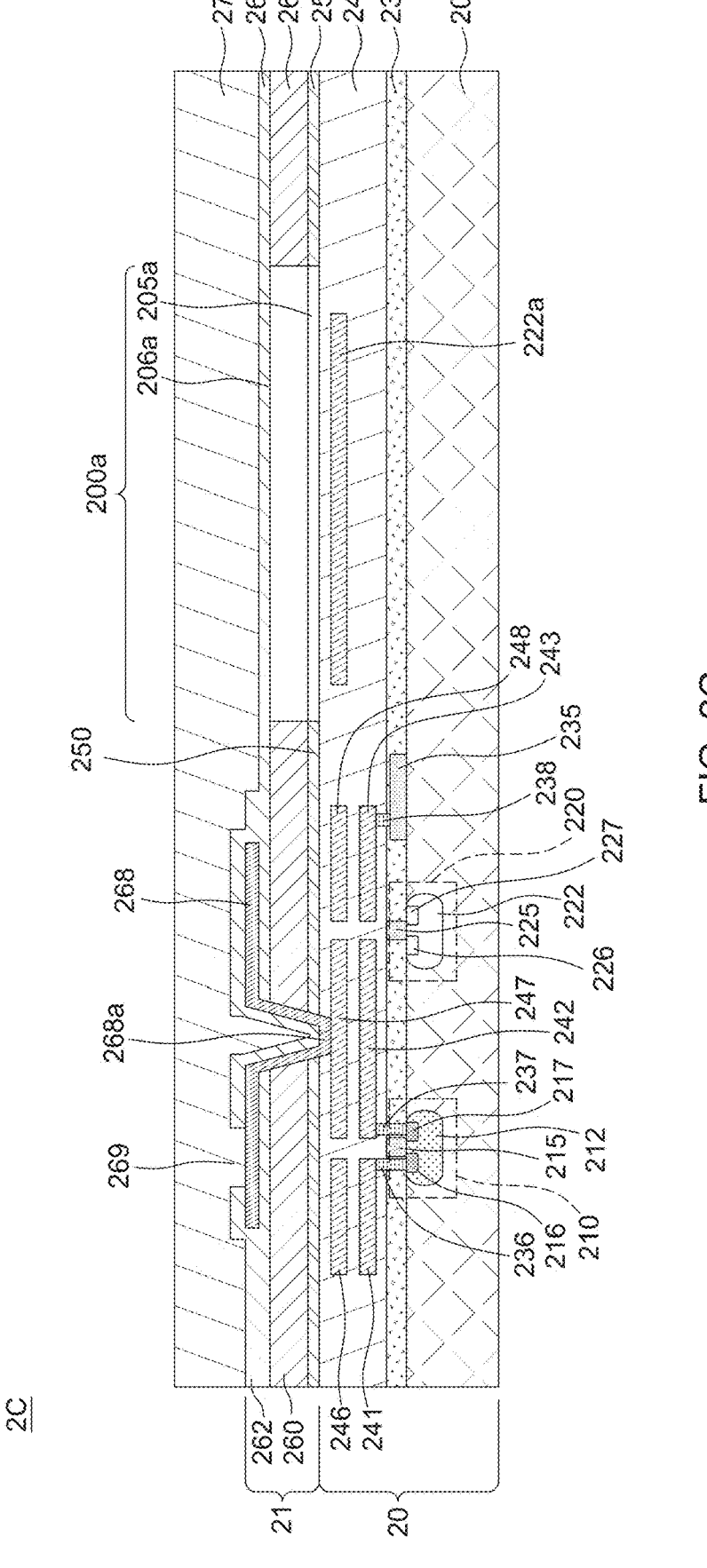
FIG. 2C is a schematic view of another semiconductor device, in accordance with some embodiments of the present disclosure.

FIG. 2C is a schematic view of the semiconductor device 2C, in accordance with some embodiments of the present disclosure. The semiconductor device 2C of FIG. 2C may be similar to the semiconductor device 2A of FIG. 2A, except for the differences described as follows.

The semiconductor device 2C may include an acoustic transducer 200a. The acoustic transducer 200a may include a membrane 206a, a space gap 205a and an electrode 222a.

The electrode 222a may be formed or embedded within the insulating layer 240. The electrode 222a may be separated from the space gap 205a. The electrode 222a may include or become a bottom electrode arranged under the membrane 206a. The membrane 206a may further include a top electrode (not shown). The top electrode could be formed within the membrane 206a. The top electrode may include, for example, the material of highly doped silicon.

In some embodiments, the acoustic transducer 200a may include a CMUT. The acoustic transducer 200a could be used to detect or obtain an image of vein and tissue of human. In some embodiments, the acoustic transducer 200a may be powered by a battery or a voltage source. In some embodiments, the vibrating frequency of the membrane 206a could be calculated or analyzed. In some embodiments, the acoustic transducer 200a may have high bandwidth and high resolution. In some embodiments, the acoustic transducer 200a may be suitable for high frequency applications. The acoustic transducer 200a may be applicable for scanning images in deep level of vein and tissue.

Figures 2D, 2E:
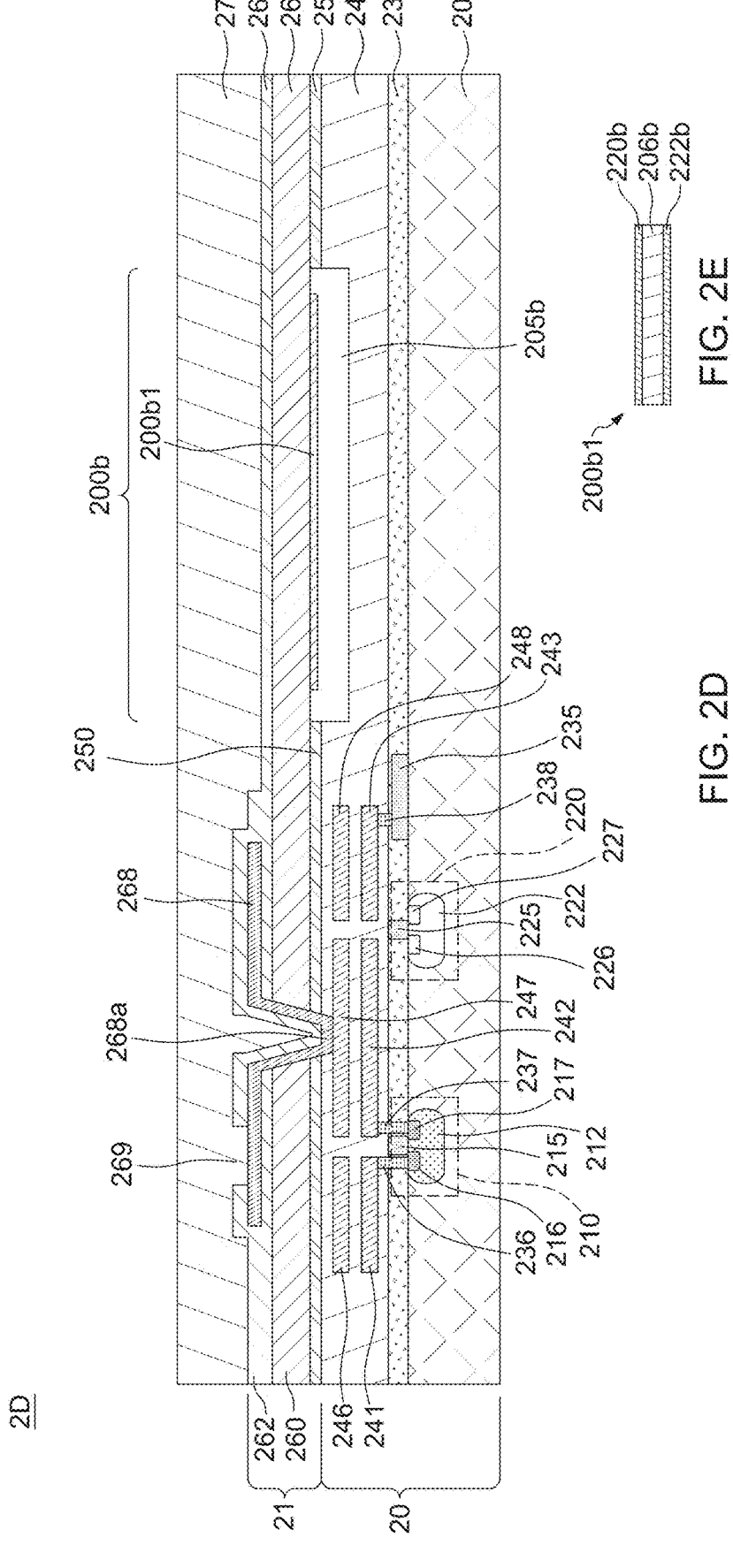
FIG. 2D is a schematic view of another semiconductor device, in accordance with some embodiments of the present disclosure.
FIG. 2E is a schematic view of an acoustic transducer of the semiconductor device, in accordance with some embodiments of the present disclosure.

FIG. 2D is a schematic view of the semiconductor device 2D, in accordance with some embodiments of the present disclosure. The semiconductor device 2D of FIG. 2D may be similar to the semiconductor device 2A of FIG. 2A, except for the differences described as follows.

The semiconductor device 2D may include an acoustic transducer 200b. The acoustic transducer 200b may include a membrane structure 200b1 and a space gap 205b. The membrane structure 200b1 may be embedded within the space gap 205b. The membrane structure 200b1 may be formed on an upper portion of the space gap 205b. The top surface of the membrane structure 200b1 may be coplanar with that of the space gap 205b.

The acoustic transducer 200b may include a PMUT. The acoustic transducer 200b could be used to detect or obtain an image of vein and tissue of human. In some embodiments, the acoustic transducer 200b may be avoid of a battery or a voltage source. In some embodiments, the vibrating frequency of the membrane 206b could be calculated or analyzed. In some embodiments, the acoustic transducer 200b may have lower bandwidth than that of the acoustic transducer 200a of FIG. 2B. In some embodiments, the acoustic transducer 200b may consume less power than that of the acoustic transducer 200a of FIG. 2B. In some embodiments, the acoustic transducer 200b may be suitable for low frequency applications. The acoustic transducer 200b may be applicable for scanning images in shallow level of vein and tissue.

FIG. 2E is a schematic view of the membrane structure 200b1 of the acoustic transducer 200b, in accordance with some embodiments of the present disclosure. The membrane structure 200b1 may include an electrode 220b, a membrane 206b and an electrode 222b. The membrane 206b may include a piezoelectric material. The membrane 206b may directly contact a bottom surface of the electrode 220b. The membrane 206b may directly contact a top surface of the electrode 222b.

Figure 3C:
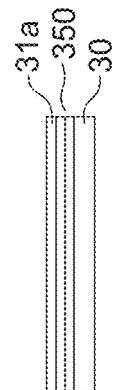
FIG. 3C is another schematic view of bonding two semiconductor devices, in accordance with some embodiments of the present disclosure.
Figure 3B:
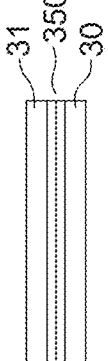
FIG. 3B is another schematic view of bonding two semiconductor devices, in accordance with some embodiments of the present disclosure.
Figure 3A:
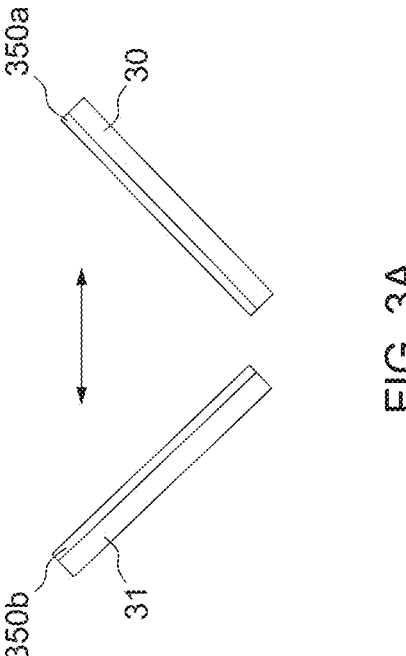
FIG. 3A is a schematic view of bonding two semiconductor devices, in accordance with some embodiments of the present disclosure.

FIGS. 3A, 3B and 3C are schematic views of bonding two semiconductor components 30 and 31, in accordance with some embodiments of the present disclosure. The semiconductor component 30 may include a bonding layer 350a. The semiconductor component 31 may include a bonding layer 350b.

In some embodiments, as shown in FIG. 3B, the semiconductor components 30 and 31 could be stacked together by attaching the bonding layers 350a and 350b. In some embodiments, the semiconductor components 30 and 31 may be bonded by utilizing a fusion bonding. In some embodiments, the semiconductor component 31 may be thinned down to become the semiconductor component 31a as shown in FIG. 3C. The thickness of the semiconductor component 31a may be smaller than that of the semiconductor component 31.

Figures 4A, 4B:
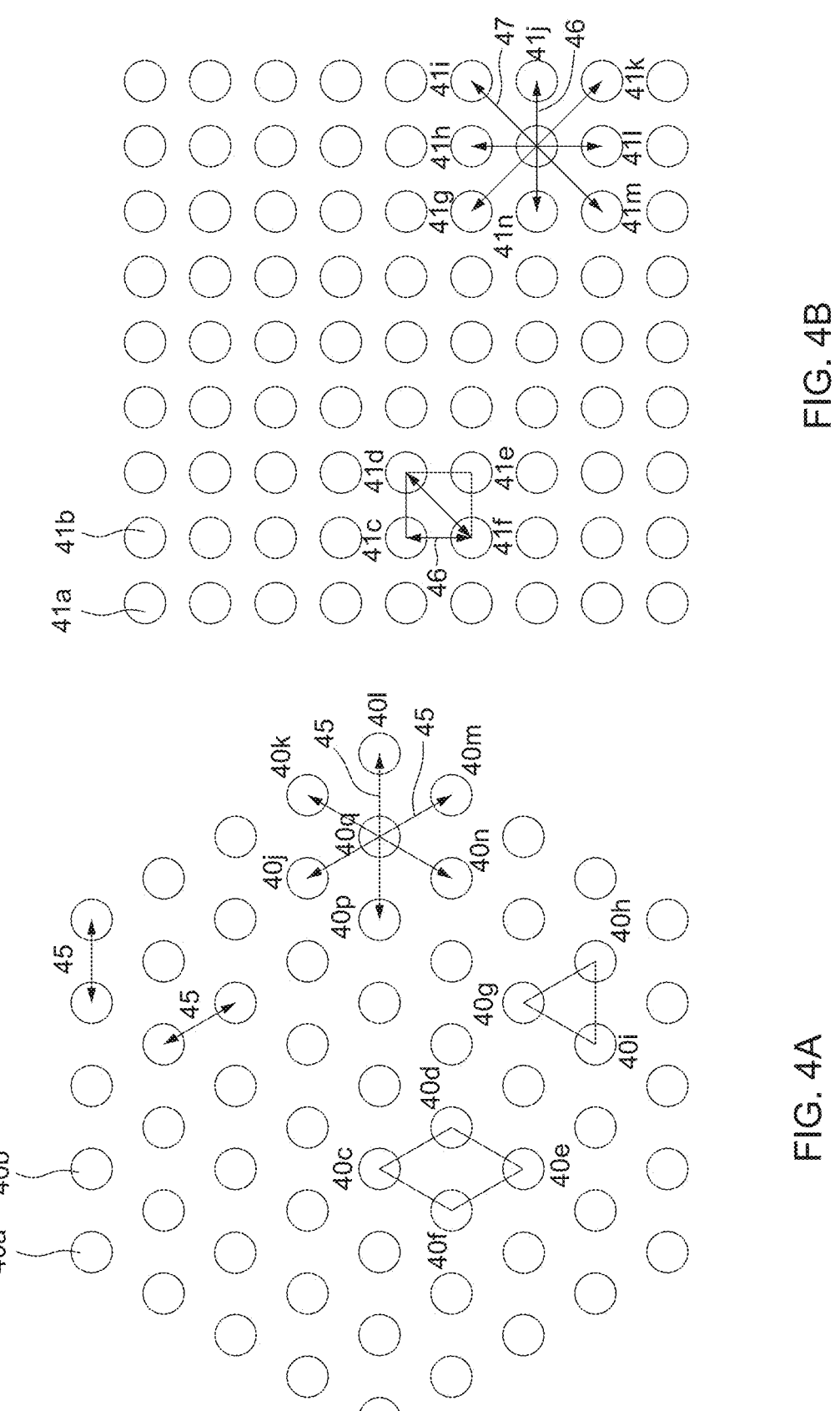
FIG. 4A is a schematic view of a semiconductor system, in accordance with some embodiments of the present disclosure.
FIG. 4B is a schematic view of another semiconductor system, in accordance with some embodiments of the present disclosure.

FIG. 4A is a schematic view of a semiconductor system 4A, in accordance with some embodiments of the present disclosure. The semiconductor system 4A may include a plurality of semiconductor devices 40a, 40b to 40q. The semiconductor devices 40a, 40b to 40q may include a CMUT or a PMUT. Each of the semiconductor devices 40a, 40b to 40q may be similar to the semiconductor device illustrated above such as the semiconductor devices 2A to 2D, and thus detailed description thereof is omitted for brevity.

In some embodiments, the semiconductor devices 40a, 40b to 40q may be distributed in a figure of triangle, diamond, square or rectangle. In some embodiments, each of the semiconductor devices 40a, 40b to 40q may be spaced apart from another by a distance 45. The distance 45 could be a predetermined distance according to or corresponding to a sound wavelength of the acoustic transducer in the semiconductor device. In some embodiments, the distance 45 may be smaller than the sound wavelength of the acoustic transducer. In some embodiments, the distance 45 may be in a range of 60% to 90% of the sound wavelength of the acoustic transducer. In some embodiments, the distance 45 may be 70% of the sound wavelength of the acoustic transducer.

As shown in FIG. 4A, the semiconductor device 40c to 40f may be provided to form a shape of diamond. In some embodiments, the semiconductor device 40g to 40i may be provided to form a shape of triangle. In some embodiments, the semiconductor device 40q may be surrounded by the semiconductor devices 40j to 40p. There could be the distance 45 between the semiconductor device 40q and each of the semiconductor devices 40j to 40p.

FIG. 4B is a schematic view of another semiconductor system 4B, in accordance with some embodiments of the present disclosure. The semiconductor system 4B may include a plurality of semiconductor devices 41a, 41b to 41p. The semiconductor devices 41a, 41b to 41p may include a CMUT or a PMUT. Each of the semiconductor devices 41a, 41b to 41p may be similar to the semiconductor device illustrated above such as the semiconductor devices 2A to 2D, and thus detailed description thereof is omitted for brevity.

As shown in FIG. 4B, the semiconductor device 41c to 41f may be provided to form a square or a rectangle. In some embodiments, the semiconductor device 41f may be spaced apart from the semiconductor device 41c by a distance 46. The distance 46 may be similar to the distance 45 of FIG. 4A. In some embodiments, the semiconductor device 41f may be spaced apart from the semiconductor device 41d by a distance 47. The distance 47 may be greater than the distance 46.

In some embodiments, the semiconductor device 41p may be surrounded by the semiconductor devices 41g to 41n. There could be the distance 46 between the semiconductor device 40p and each of the semiconductor devices 41h, 41j, 41l and 41n. In addition, there could be the distance 47 between the semiconductor device 40p and each of the semiconductor devices 41i, 41k, 41m and 41g.

FIG. 5A to FIG. 5H are schematic views of a semiconductor system, in accordance with some embodiments of the present disclosure. In some embodiments, as shown in FIG.

5A, the semiconductor system 5A may include a plurality of semiconductor devices, such as the semiconductor devices 50a, 50b and 50c. The semiconductor devices in FIG. 5A may be distributed in a figure of hexagon. Each of the semiconductor devices in FIG. 5A may include a CMUT.

Figure 5B:
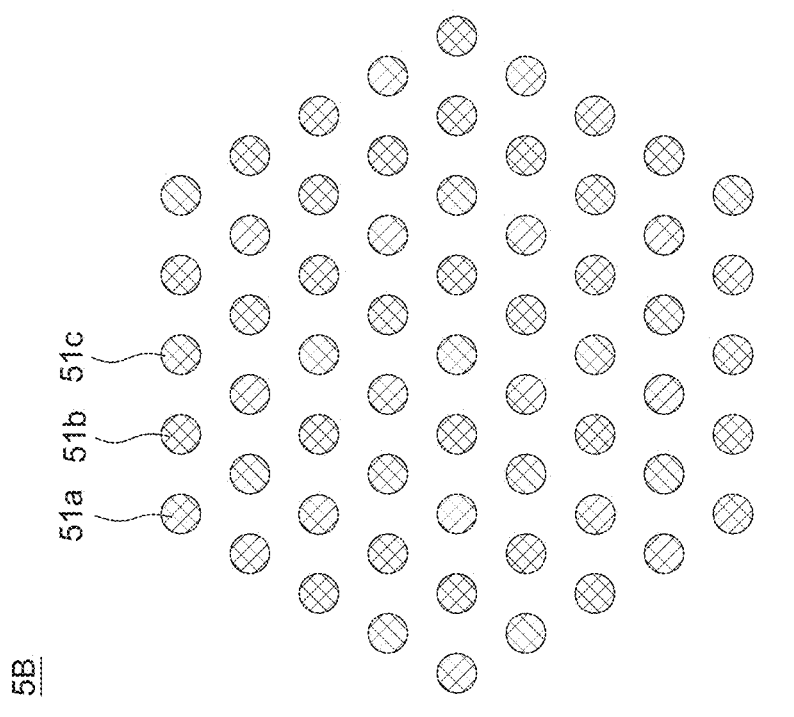
FIG. 5A to FIG. 5H are schematic views of a semiconductor system, in accordance with some embodiments of the present disclosure.
Figure 5A:
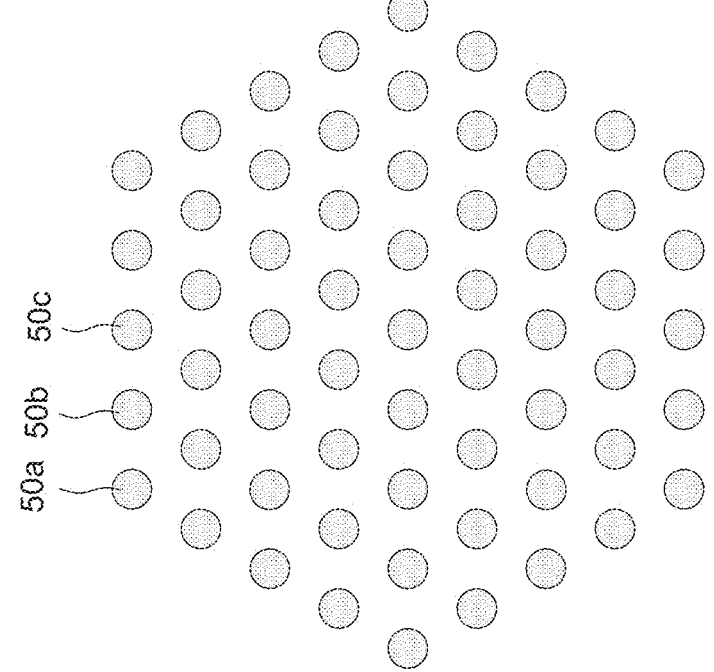

In some embodiments, as shown in FIG. 5B, the semiconductor system 5B may include a plurality of semiconductor devices, such as the semiconductor devices 51a, 51b and 51c. The semiconductor devices in FIG. 5B may be distributed in a figure of hexagon. Each of the semiconductor devices in FIG. 5B may include a PMUT.

Figure 5D:
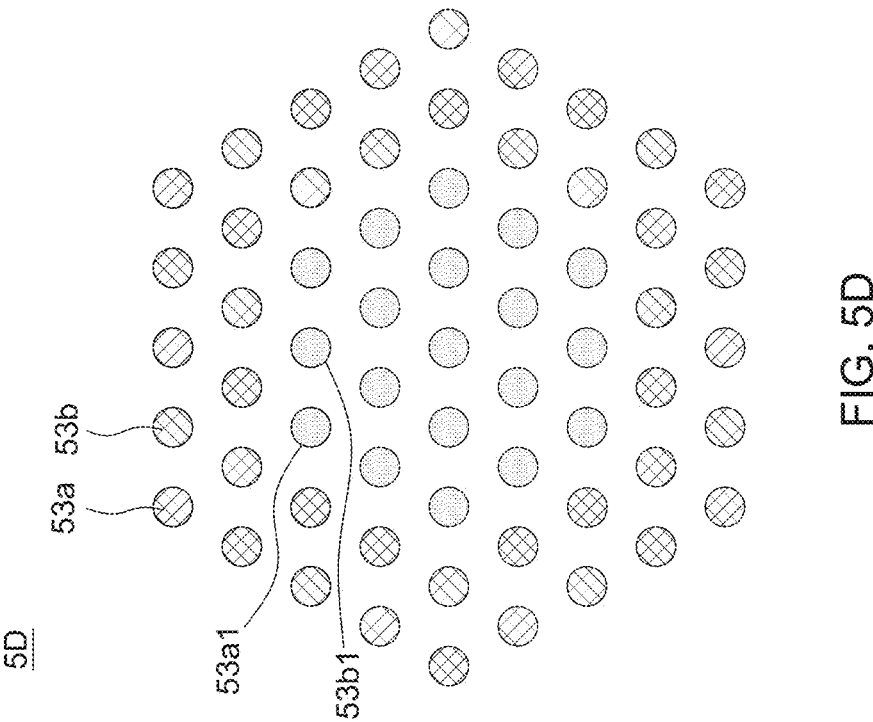
Figure 5C:
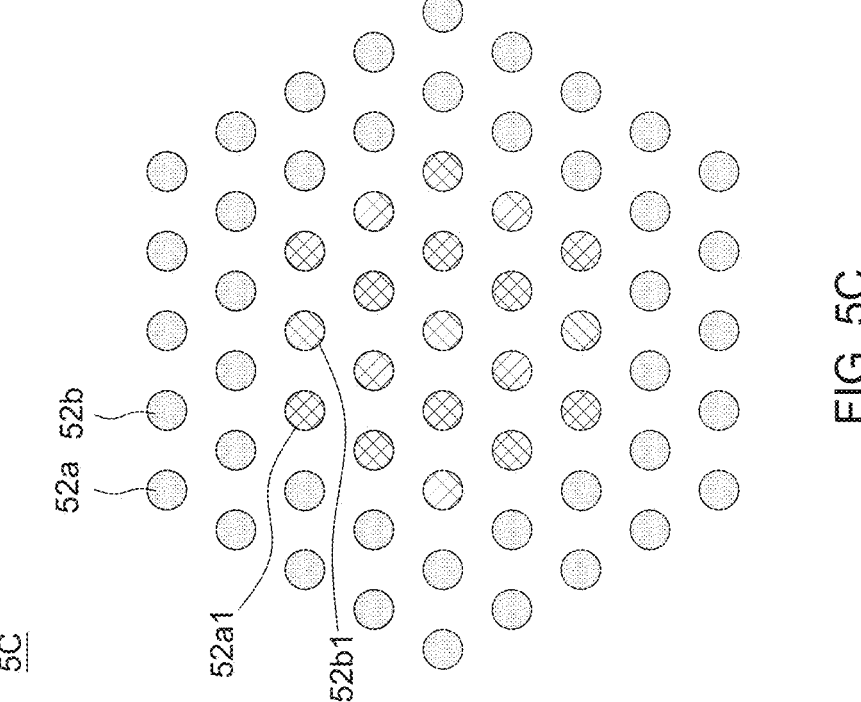

In some embodiments, as shown in FIG. 5C, the semiconductor system 5C may include a plurality of semiconductor devices, such as the semiconductor devices 52a, 52b, 52a1 and 52b1. The semiconductor devices in FIG. 5C may be distributed in a figure of hexagon. The semiconductor devices in FIG. 5C may include a CMUT or a PMUT. The semiconductor devices with a PMUT (such as the semiconductor devices 52a1 and 52b1) are encircled or surrounded by the semiconductor devices with a CMUT (such as the semiconductor devices 52a and 52b).

In some embodiments, as shown in FIG. 5D, the semiconductor system 5D may include a plurality of semiconductor devices, such as the semiconductor devices 53a, 53b, 53a1 and 53b1. The semiconductor devices in FIG. 5D may be distributed in a figure of hexagon. The semiconductor devices in FIG. 5D may include a CMUT or a PMUT. The semiconductor devices with a CMUT (such as the semiconductor devices 53a1 and 53b1) are encircled or surrounded by the semiconductor devices with a PMUT (such as the semiconductor devices 53a and 53b).

Figure 5F:
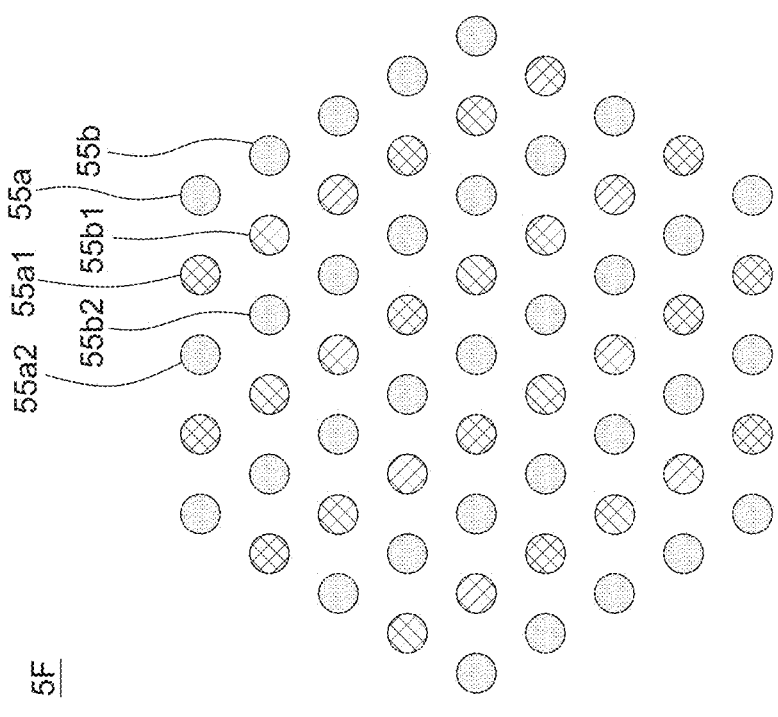
Figure 5E:
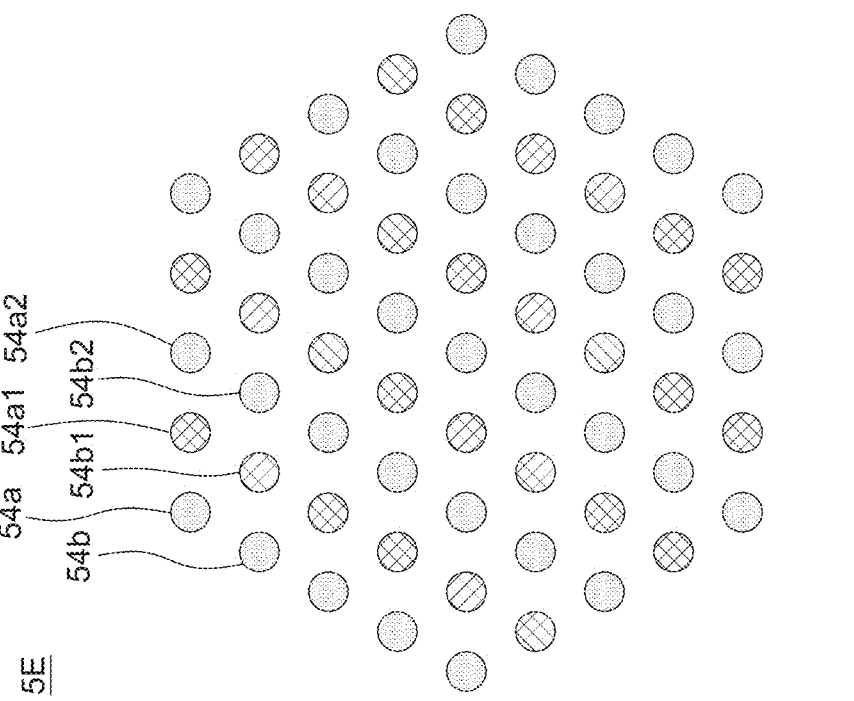

In some embodiments, as shown in FIG. 5E, the semiconductor system 5E may include a plurality of semiconductor devices, such as the semiconductor devices 54a, 54b, 54a1, 54b1, 54a2 and 54b2. The semiconductor devices in FIG. 5E may be distributed in a figure of hexagon. The semiconductor devices in FIG. 5E may include a CMUT or a PMUT. The semiconductor devices with a CMUT (such as the semiconductor devices 54a and 54b) may be formed in a line. The semiconductor devices with a PMUT (such as the semiconductor devices 54a1 and 54b1) may be formed in another line. The semiconductor devices with the CMUT may be interleaved with the semiconductor devices with the PMUT in a tilting direction.

In some embodiments, as shown in FIG. 5F, the semiconductor system 5F may include a plurality of semiconductor devices, such as the semiconductor devices 55a, 55b, 55a1, 55b1, 55a2 and 55b2. The semiconductor devices in FIG. 5F may be distributed in a figure of hexagon. The semiconductor devices in FIG. 5F may include a CMUT or a PMUT. The semiconductor devices with a CMUT (such as the semiconductor devices 55a and 55b) may be formed in a line. The semiconductor devices with a PMUT (such as the semiconductor devices 55a1 and 55b1) may be formed in another line. The semiconductor devices with the CMUT may be interleaved with the semiconductor devices with the PMUT in a tilting direction.

Figures 5G, 5H:
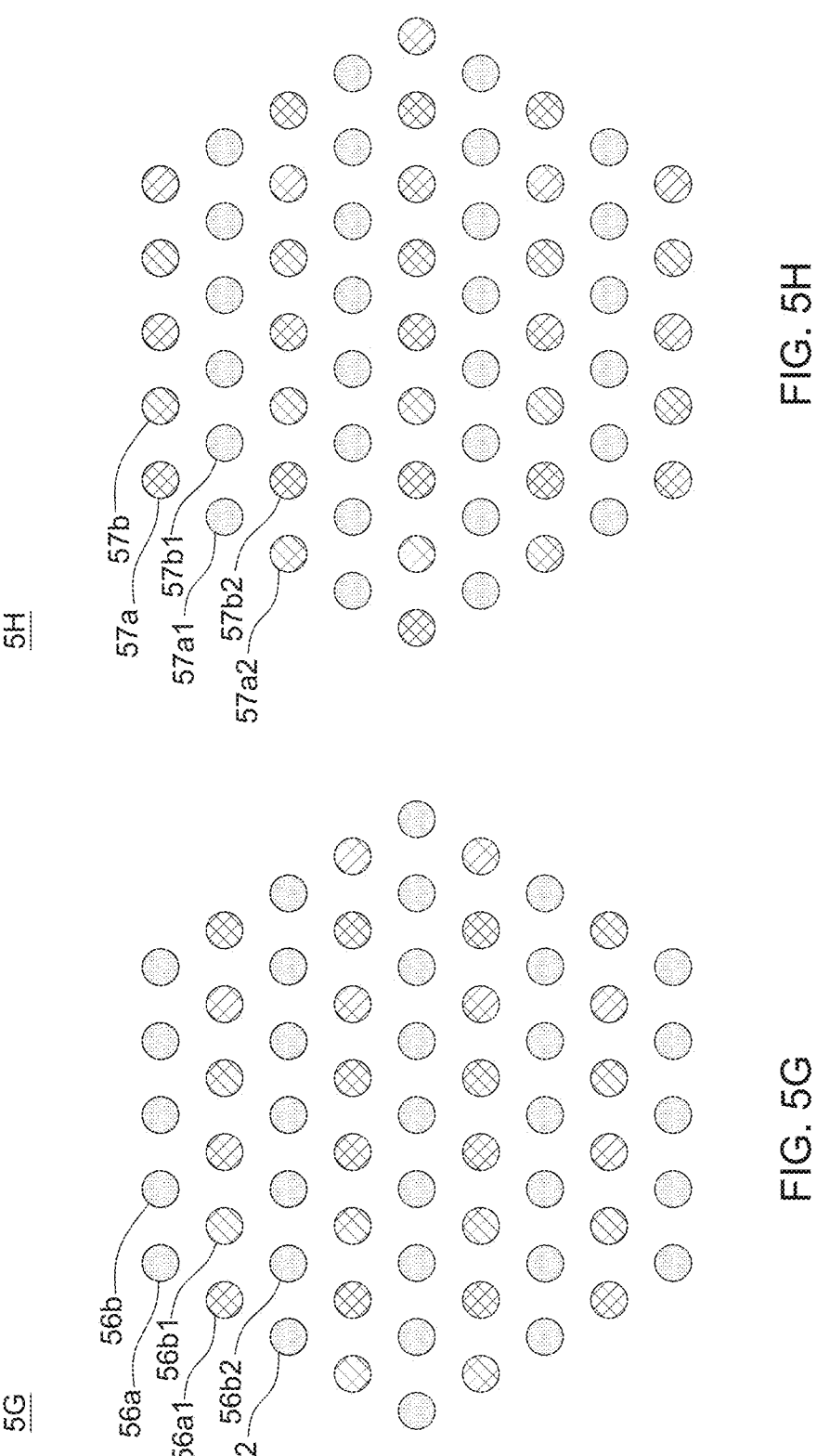

In some embodiments, as shown in FIG. 5G, the semiconductor system 5G may include a plurality of semiconductor devices, such as the semiconductor devices 56a, 56b, 56a1, 56b1, 56a2 and 56b2. The semiconductor devices in FIG. 5G may be distributed in a figure of hexagon. The semiconductor devices in FIG. 5G may include a CMUT or a PMUT. The semiconductor devices with a CMUT (such as the semiconductor devices 56a and 56b) may be formed in a line. The semiconductor devices with a PMUT (such as the semiconductor devices 56a1 and 56b1) may be formed in another line. The semiconductor devices with the CMUT may be interleaved with the semiconductor devices with the PMUT in a horizontal direction. The semiconductor devices with the CMUT may be lined in order with the semiconductor devices with the PMUT.

In some embodiments, as shown in FIG. 5H, the semiconductor system 5H may include a plurality of semiconductor devices, such as the semiconductor devices 57a, 57b, 57a1, 57b1, 57a2 and 57b2. The semiconductor devices in FIG. 5H may be distributed in a figure of hexagon. The semiconductor devices in FIG. 5H may include a CMUT or a PMUT. The semiconductor devices with a PMUT (such as the semiconductor devices 57a and 57b) may be formed in a line. The semiconductor devices with a CMUT (such as the semiconductor devices 57a1 and 57b1) may be formed in another line. The semiconductor devices with the CMUT may be interleaved with the semiconductor devices with the PMUT in a horizontal direction. The semiconductor devices with the CMUT may be lined in order with the semiconductor devices with the PMUT.

Figures 6A, 6B:
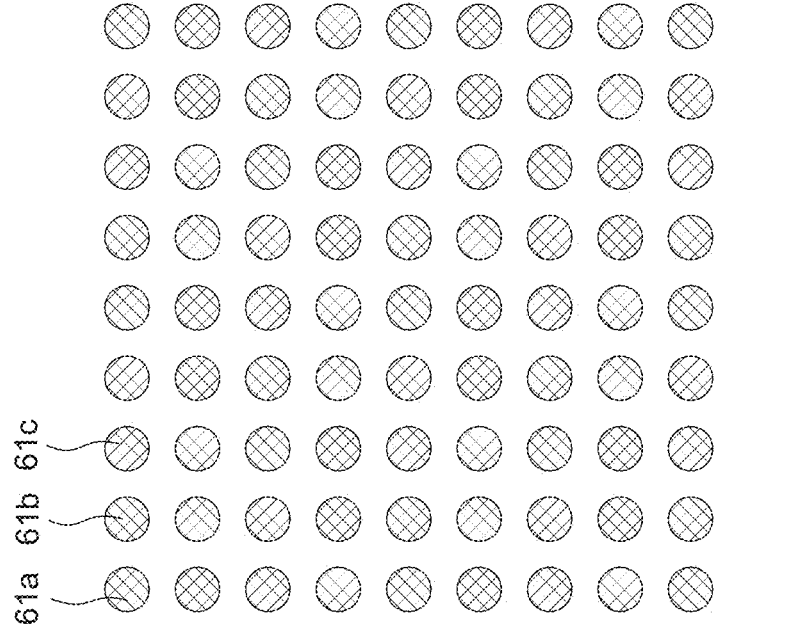
FIG. 6A to FIG. 6F are schematic views of a semiconductor system, in accordance with some embodiments of the present disclosure.

FIG. 6A to FIG. 6F are schematic views of a semiconductor system, in accordance with some embodiments of the present disclosure. In some embodiments, as shown in FIG. 6A, the semiconductor system 6A may include a plurality of semiconductor devices, such as the semiconductor devices 60a, 60b and 60c. The semiconductor devices in FIG. 6A may be distributed in a figure of square. Each of the semiconductor devices in FIG. 6A may include a CMUT.

In some embodiments, as shown in FIG. 6B, the semiconductor system 6B may include a plurality of semiconductor devices, such as the semiconductor devices 61a, 61b and 61c. The semiconductor devices in FIG. 6B may be distributed in a figure of square. Each of the semiconductor devices in FIG. 6B may include a PMUT.

Figure 6D:
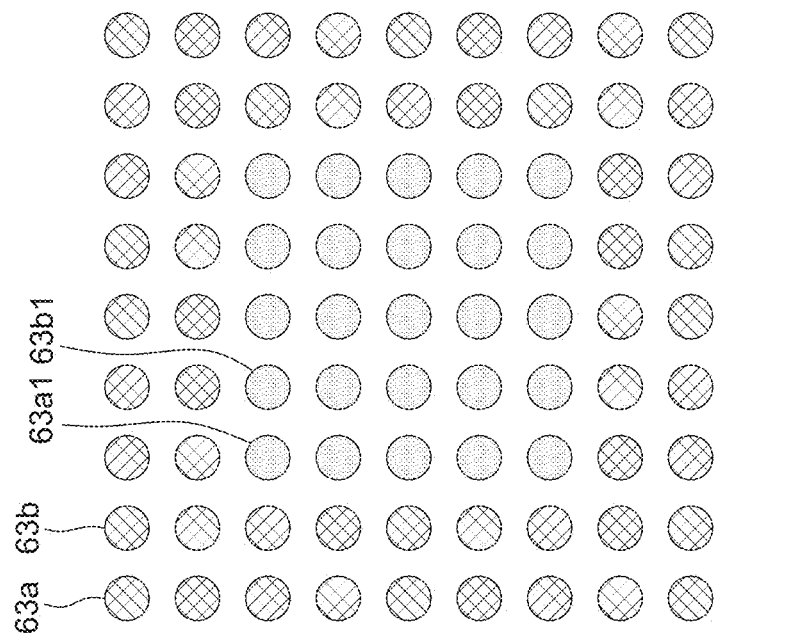
Figure 6C:
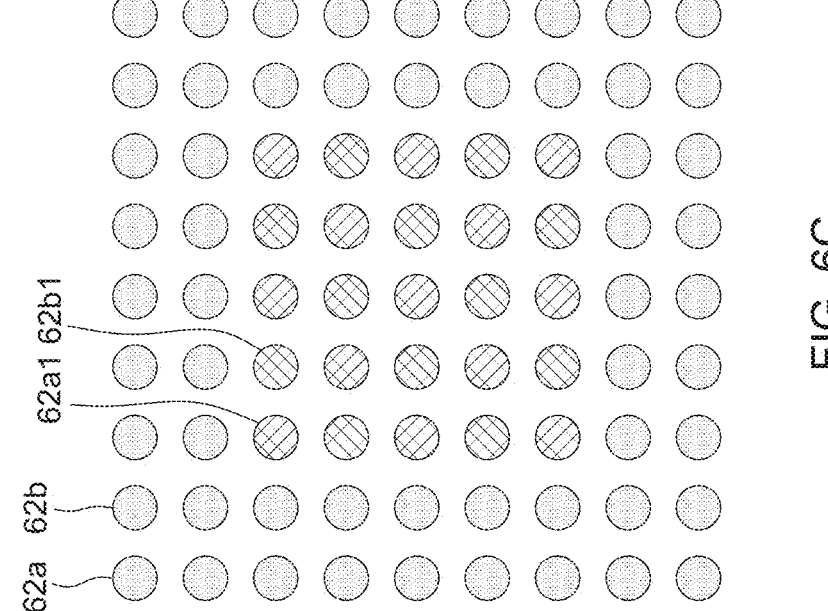

In some embodiments, as shown in FIG. 6C, the semiconductor system 6C may include a plurality of semiconductor devices, such as the semiconductor devices 62a, 62b, 62a1 and 62b1. The semiconductor devices in FIG. 6C may be distributed in a figure of square. The semiconductor devices in FIG. 6C may include a CMUT or a PMUT. The semiconductor devices with a PMUT (such as the semiconductor devices 62a1 and 62b1) are encircled or surrounded by the semiconductor devices with a CMUT (such as the semiconductor devices 62a and 62b).

In some embodiments, as shown in FIG. 6D, the semiconductor system 6D may include a plurality of semiconductor devices, such as the semiconductor devices 63a, 63b, 63a1 and 63b1. The semiconductor devices in FIG. 6D may be distributed in a figure of square. The semiconductor devices in FIG. 6D may include a CMUT or a PMUT. The semiconductor devices with a CMUT (such as the semiconductor devices 63a1 and 63b1) are encircled or surrounded by the semiconductor devices with a PMUT (such as the semiconductor devices 63a and 63b).

Figure 6F:
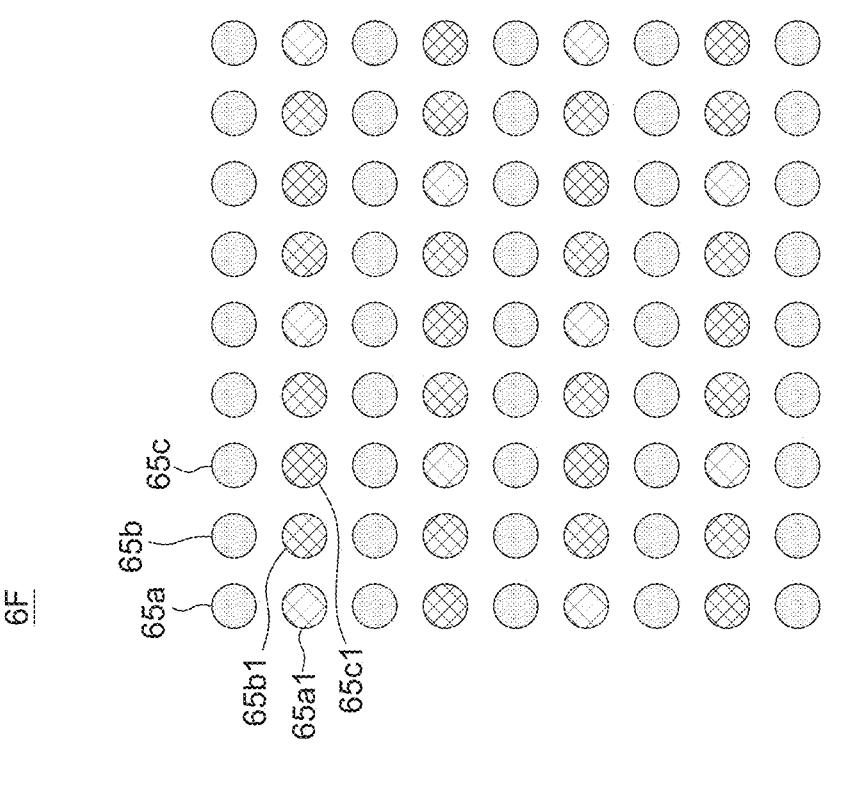
Figure 6E:
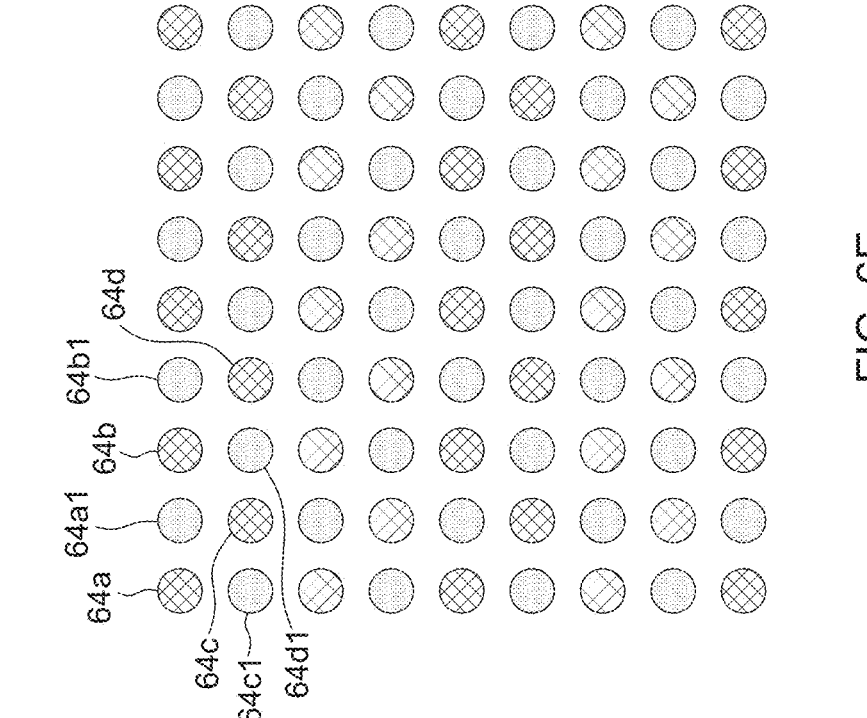

In some embodiments, as shown in FIG. 6E, the semiconductor system 6E may include a plurality of semiconductor devices, such as the semiconductor devices 64a, 64b, 64c, 64d, 64a1, 64b1, 64c1 and 64d1. The semiconductor devices in FIG. 6E may be distributed in a figure of square. The semiconductor devices in FIG. 6E may include a CMUT or a PMUT. Each of the semiconductor devices with a CMUT (such as the semiconductor devices 64a1, 64b1, 64c1 and 64d1) may be interleaved with each of the semiconductor devices with a PMUT (such as the semiconductor devices 64a, 64b, 64c and 64d).

In some embodiments, as shown in FIG. 6F, the semiconductor system 6F may include a plurality of semiconductor devices, such as the semiconductor devices 65a, 65b, 65c, 65a1, 65b1 and 65c1. The semiconductor devices in FIG. 6F may be distributed in a figure of square. The semiconductor devices in FIG. 6F may include a CMUT or a PMUT. The semiconductor devices with a CMUT (such as the semiconductor devices 65a, 65b and 65c) may be formed in a line. The semiconductor devices with a PMUT (such as the semiconductor devices 65a1, 65b1 and 65c1) may be formed in another line. The semiconductor devices with the CMUT may be interleaved with the semiconductor devices with the PMUT in a horizontal direction. The semiconductor devices with the CMUT may be lined in order with the semiconductor devices with the PMUT.

Figures 7A, 7B, 7C:
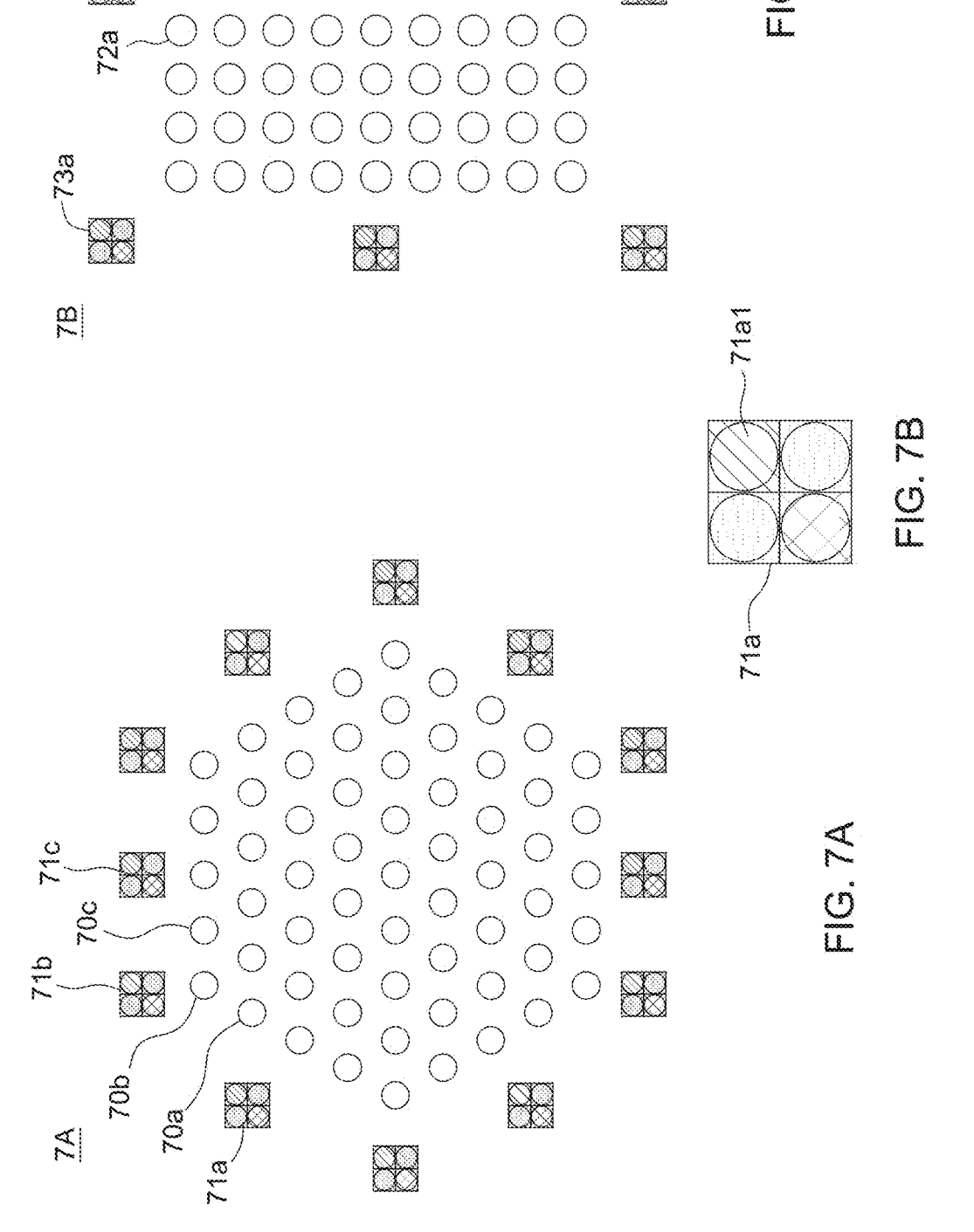
FIG. 7A is schematic views of a semiconductor system, in accordance with some embodiments of the present disclosure.
FIG. 7B is schematic views of a light emitting device, in accordance with some embodiments of the present disclosure.
FIG. 7C is schematic views of a semiconductor system, in accordance with some embodiments of the present disclosure.

FIG. 7A is schematic views of a semiconductor system 7A, in accordance with some embodiments of the present disclosure. The semiconductor system 7A may include a plurality of semiconductor devices and a plurality of light emitting devices. The semiconductor devices in FIG. 7A may include a CMUT or a PMUT. The semiconductor devices in FIG. 7A may be distributed in a figure of hexagon.

In some embodiments, the semiconductor devices (such as the semiconductor devices 70a, 70b and 70c) may be encircled or surrounded by the light emitting devices (such as the light emitting devices 71a, 71b and 71c). The light emitting devices 71a, 71b and 71c may be used to generate or transmit visible light, such as red light, green light and blue light. The light emitting devices 71a, 71b and 71c may be used to generate or transmit visible light, for example, in a wavelength range of 400 nm to 800 nm. The light emitting devices 71a, 71b and 71c may include visible light micro-LEDs. The light emitting devices 71a, 71b and 71c may be used to detect or obtain an image of skin of human.

FIG. 7B is schematic views of the light emitting device 72a, in accordance with some embodiments of the present disclosure. The light emitting device 72a may include one or more lens 71a1. In some embodiments, the lens 71a1 may include a micro-lens. In some embodiments, the lens 71a1 may be used to focus the visible light to a certain point or a certain depth to improve the detecting accuracy.

FIG. 7C is schematic views of a semiconductor system 7B, in accordance with some embodiments of the present disclosure. The semiconductor devices in FIG. 7C may be distributed in a figure of square. In some embodiments, the semiconductor devices (such as the semiconductor devices 72a, 72b and 72c) may be encircled or surrounded by the light emitting devices (such as the light emitting devices 73a, 73b and 73c). The light emitting devices 73a, 73b and 73c may be used to generate or transmit visible light, such as red light, green light and blue light. The light emitting devices 73a, 73b and 73c may be used to generate or transmit visible light, for example, in a wavelength range of 400 nm to 800 nm. The light emitting devices 73a, 73b and 73c may include visible light micro-LEDs. The light emitting devices 73a, 73b and 73c may be used to detect or obtain an image of skin of human.

Figures 8A, 8B, 8C:
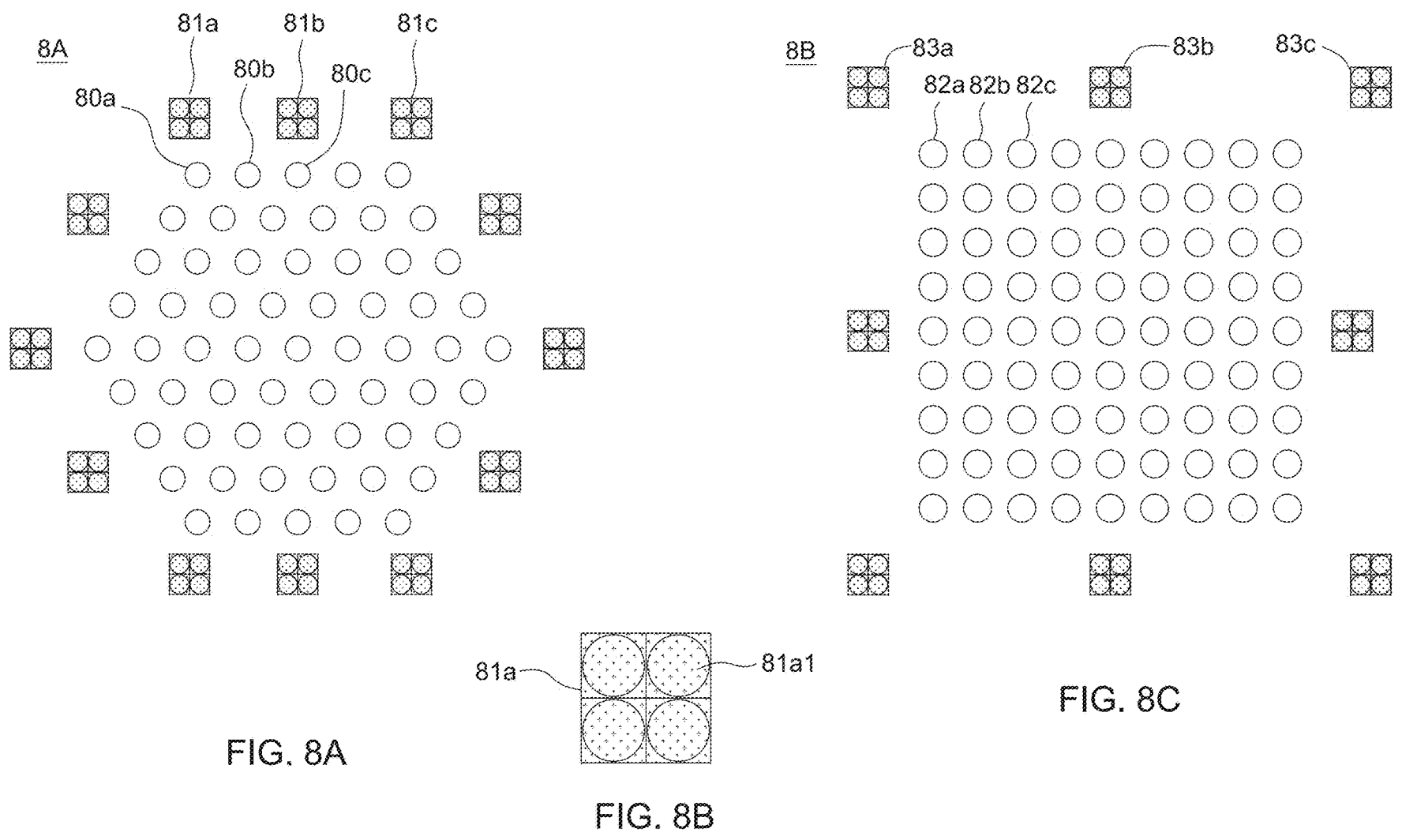

FIG. 8A is schematic views of a semiconductor system 8A, in accordance with some embodiments of the present disclosure. The semiconductor system 8A may include a plurality of semiconductor devices and a plurality of light emitting devices. The semiconductor devices in FIG. 8A may include a CMUT or a PMUT. The semiconductor devices in FIG. 8A may be distributed in a figure of hexagon.

In some embodiments, the semiconductor devices (such as the semiconductor devices 80a, 80b and 80c) may be encircled or surrounded by the light emitting devices (such as the light emitting devices 81a, 81b and 81c). The light emitting devices 81a, 81b and 81c may be used to generate or transmit ultraviolet light. The light emitting devices 81*a*, 81*b* and 81*c* may be used to generate or transmit ultraviolet light, for example, in a wavelength range of 100 nm to 400 nm. The light emitting devices 81*a*, 81*b* and 81*c* may include ultraviolet light micro-LEDs. The light emitting devices 81*a*, 81*b* and 81*c* may be used to detect or obtain an image of skin of human.

FIG. 8B is schematic views of the light emitting device 82*a*, in accordance with some embodiments of the present disclosure. The light emitting device 82*a* may include one or more lens 81*a*1. In some embodiments, the lens 81*a*1 may include a micro-lens. In some embodiments, the lens 81*a*1 may be used to focus the ultraviolet light to a certain point or a certain depth to improve the detecting accuracy.

FIG. 8C is schematic views of a semiconductor system 8B, in accordance with some embodiments of the present disclosure. The semiconductor devices in FIG. 8C may be distributed in a figure of square. In some embodiments, the semiconductor devices (such as the semiconductor devices 82*a*, 82*b* and 82*c*) may be encircled or surrounded by the light emitting devices (such as the light emitting devices 83*a*, 83*b* and 83*c*). The light emitting devices 83*a*, 83*b* and 83*c* may be used to generate or transmit ultraviolet light. The light emitting devices 83*a*, 83*b* and 83*c* may be used to generate or transmit ultraviolet light, for example, in a wavelength range of 100 nm to 400 nm. The light emitting devices 83*a*, 83*b* and 83*c* may include ultraviolet light micro-LEDs. The light emitting devices 83*a*, 83*b* and 83*c* may be used to detect or obtain an image of skin of human.

Figures 9A, 9B, 9C:
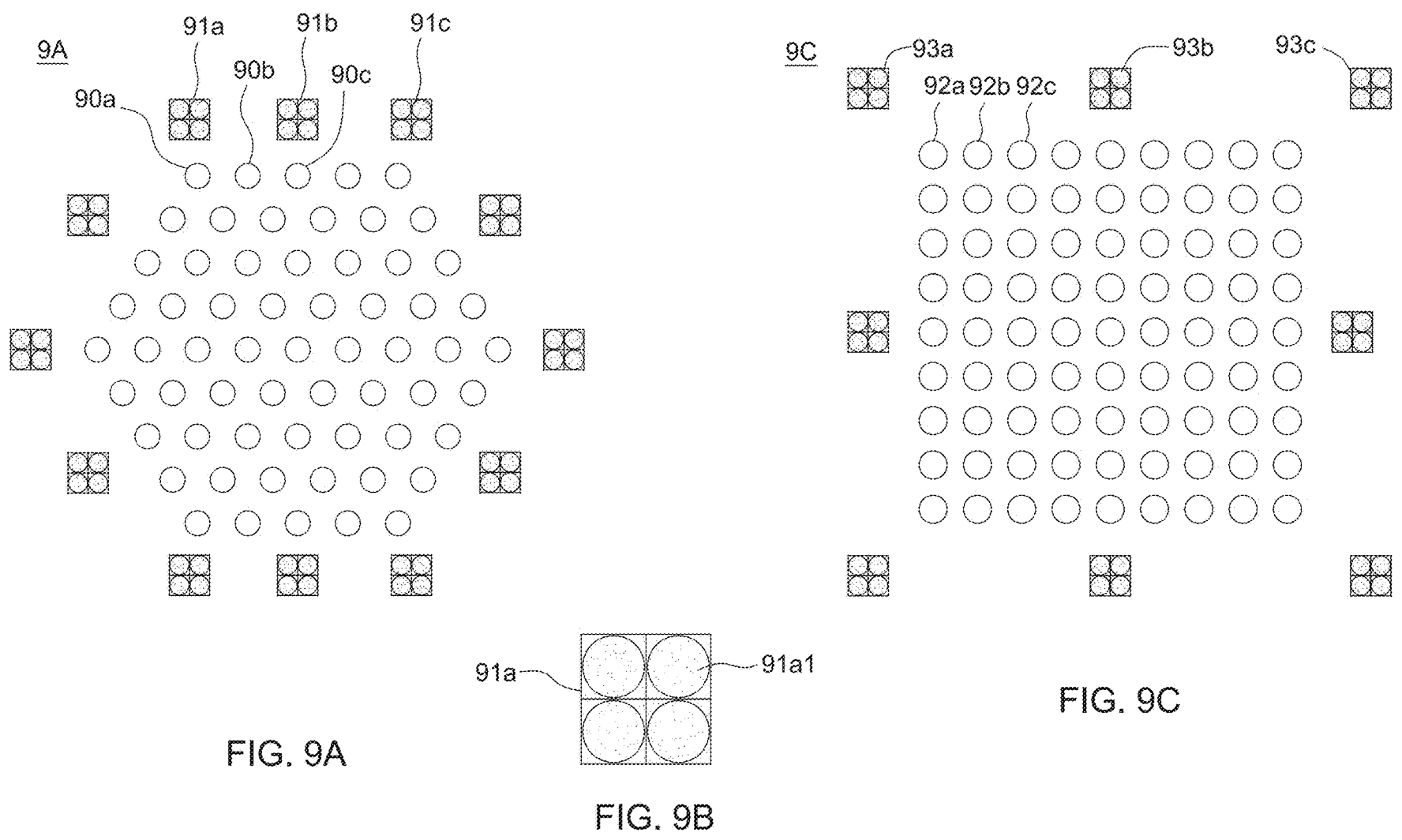

FIG. 9A is schematic views of a semiconductor system 9A, in accordance with some embodiments of the present disclosure. The semiconductor system 9A may include a plurality of semiconductor devices and a plurality of light emitting devices. The semiconductor devices in FIG. 9A may include a CMUT or a PMUT. The semiconductor devices in FIG. 9A may be distributed in a figure of hexagon.

In some embodiments, the semiconductor devices (such as the semiconductor devices 90*a*, 90*b* and 90*c*) may be encircled or surrounded by the light emitting devices (such as the light emitting devices 91*a*, 91*b* and 91*c*). The light emitting devices 91*a*, 91*b* and 91*c* may be used to generate or transmit near infrared light. The light emitting devices 91*a*, 91*b* and 91*c* may be used to generate or transmit near infrared light, for example, in a wavelength range of 800 nm to 1200 nm. The light emitting devices 91*a*, 91*b* and 91*c* may include near infrared light micro-LEDs. The light emitting devices 91*a*, 91*b* and 91*c* may be used to detect or obtain an image of skin of human.

FIG. 9B is schematic views of the light emitting device 92*a*, in accordance with some embodiments of the present disclosure. The light emitting device 92*a* may include one or more lens 91*a*1. In some embodiments, the lens 91*a*1 may include a micro-lens. In some embodiments, the lens 91*a*1 may be used to focus the near infrared light to a certain point or a certain depth to improve the detecting accuracy.

FIG. 9C is schematic views of a semiconductor system 9B, in accordance with some embodiments of the present disclosure. The semiconductor devices in FIG. 9C may be distributed in a figure of square. In some embodiments, the semiconductor devices (such as the semiconductor devices 92*a*, 92*b* and 92*c*) may be encircled or surrounded by the light emitting devices (such as the light emitting devices 93*a*, 93*b* and 93*c*). The light emitting devices 93*a*, 93*b* and 93*c* may be used to generate or transmit near infrared light. The light emitting devices 93*a*, 93*b* and 93*c* may be used to generate or transmit near infrared light, for example, in a wavelength range of 800 nm to 1200 nm. The light emitting devices 93*a*, 93*b* and 93*c* may include near infrared light micro-LEDs. The light emitting devices 93*a*, 93*b* and 93*c* may be used to detect or obtain an image of skin of human.

Figure 10A:
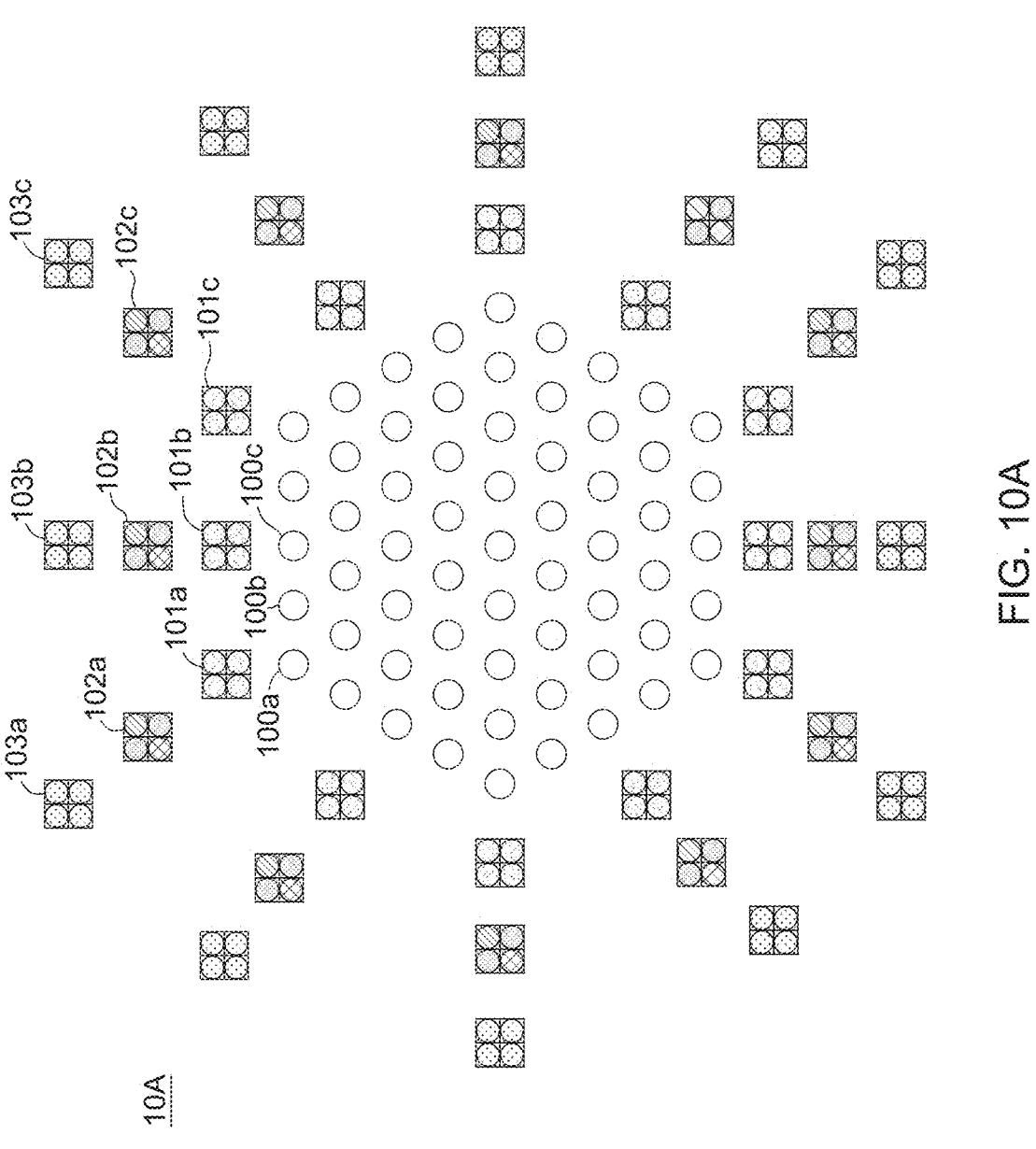
FIG. 10A is a schematic view of a semiconductor system, in accordance with some embodiments of the present disclosure.

FIG. 10A is a schematic view of a semiconductor system 10A, in accordance with some embodiments of the present disclosure. The semiconductor devices in FIG. 10A may be distributed in a figure of hexagon. In some embodiments, the semiconductor devices (such as the semiconductor devices 100*a*, 100*b* and 100*c*) may be encircled or surrounded by the light emitting devices (such as the light emitting devices 101*a*, 101*b* and 101*c*). The light emitting devices 101*a*, 101*b* and 101*c* may be used to generate or transmit near infrared lights. The light emitting devices 101*a*, 101*b* and 101*c* may include near infrared micro-LEDs.

In some embodiments, the light emitting devices (such as the light emitting devices 101*a*, 101*b* and 101*c*) may be encircled or surrounded by the light emitting devices (such as the light emitting devices 102*a*, 102*b* and 102*c*). The light emitting devices 102*a*, 102*b* and 102*c* may be used to generate or transmit visible lights. The light emitting devices 102*a*, 102*b* and 102*c* may include visible light micro-LEDs.

In some embodiments, the light emitting devices (such as the light emitting devices 102*a*, 102*b* and 102*c*) may be encircled or surrounded by the light emitting devices (such as the light emitting devices 103*a*, 103*b* and 103*c*). The light emitting devices 103*a*, 103*b* and 103*c* may be used to generate or transmit ultraviolet lights. The light emitting devices 103*a*, 103*b* and 103*c* may ultraviolet visible light micro-LEDs.

Figure 10B:
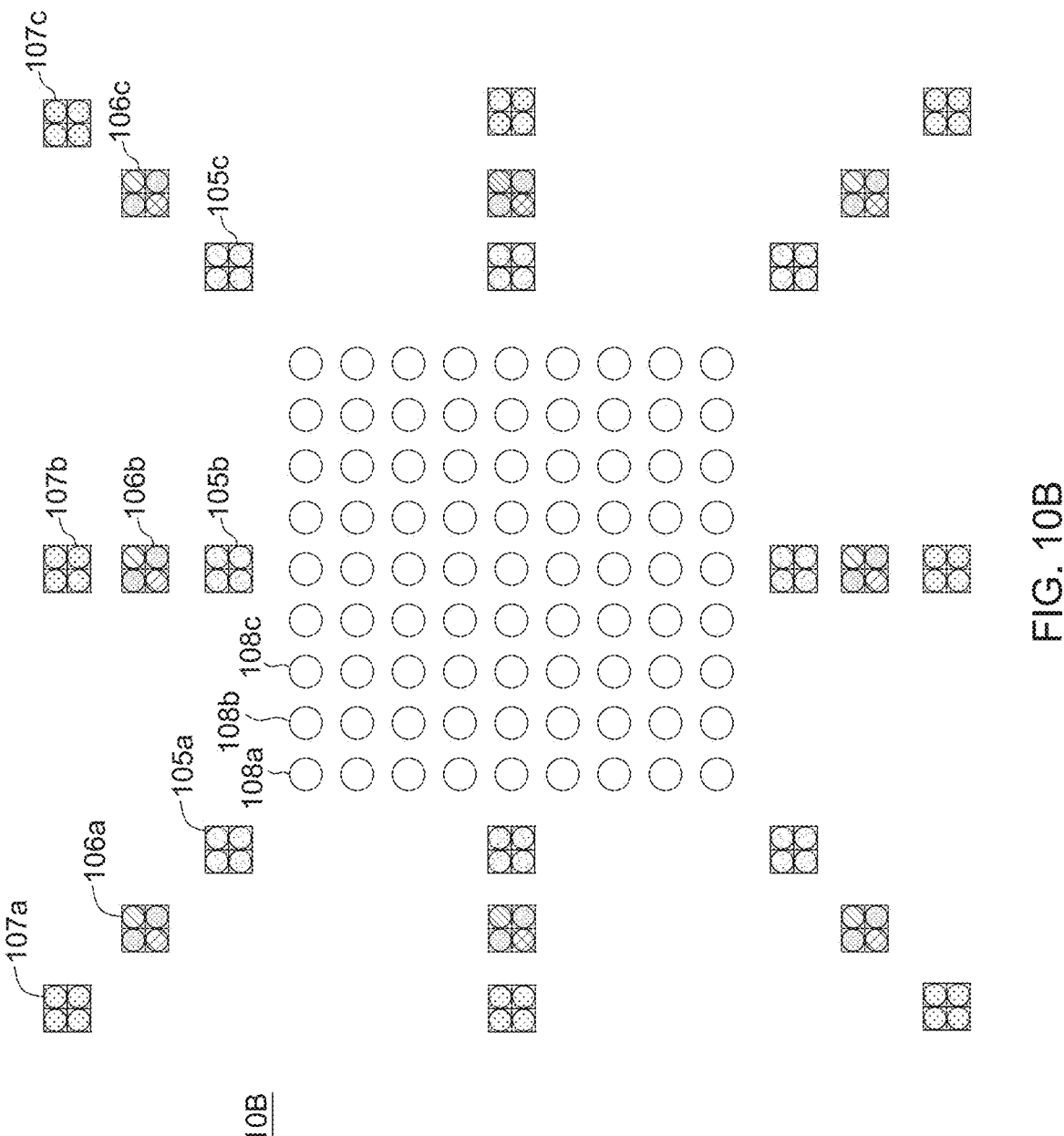
FIG. 10B is a schematic view of another semiconductor system, in accordance with some embodiments of the present disclosure.

FIG. 10B is a schematic view of another semiconductor system 10B, in accordance with some embodiments of the present disclosure. The semiconductor devices in FIG. 10B may be distributed in a figure of square. In some embodiments, the semiconductor devices (such as the semiconductor devices 108*a*, 108*b* and 108*c*) may be encircled or surrounded by the light emitting devices (such as the light emitting devices 105*a*, 105*b* and 105*c*). The light emitting devices 105*a*, 105*b* and 105*c* may be used to generate or transmit near infrared lights. The light emitting devices 105*a*, 105*b* and 105*c* may include near infrared micro-LEDs.

In some embodiments, the light emitting devices (such as the light emitting devices 105*a*, 105*b* and 105*c*) may be encircled or surrounded by the light emitting devices (such as the light emitting devices 106*a*, 106*b* and 106*c*). The light emitting devices 106*a*, 106*b* and 106*c* may be used to generate or transmit visible lights. The light emitting devices 106*a*, 106*b* and 106*c* may include visible light micro-LEDs.

In some embodiments, the light emitting devices (such as the light emitting devices 106*a*, 106*b* and 106*c*) may be encircled or surrounded by the light emitting devices (such as the light emitting devices 107*a*, 107*b* and 107*c*). The light emitting devices 107*a*, 107*b* and 107*c* may be used to generate or transmit ultraviolet lights. The light emitting devices 107*a*, 107*b* and 107*c* may ultraviolet visible light micro-LEDs.

As illustrated in the embodiments of FIG. 7A to FIG. 10B, the semiconductor device with photoacoustic imaging or ultrasound-based imaging and the light-emitting device with light-based imaging could be combined by the semiconductor system provided by the present disclosure. Therefore, the proposed semiconductor system can provide various advantages on both photoacoustic imaging and light-based imaging. The proposed semiconductor system can be used to differentiate between soft tissue structures and improve the accuracy of the imaging. Furthermore, the limited penetration depths due to the scattering of light can also be reduced.

Figure 11:
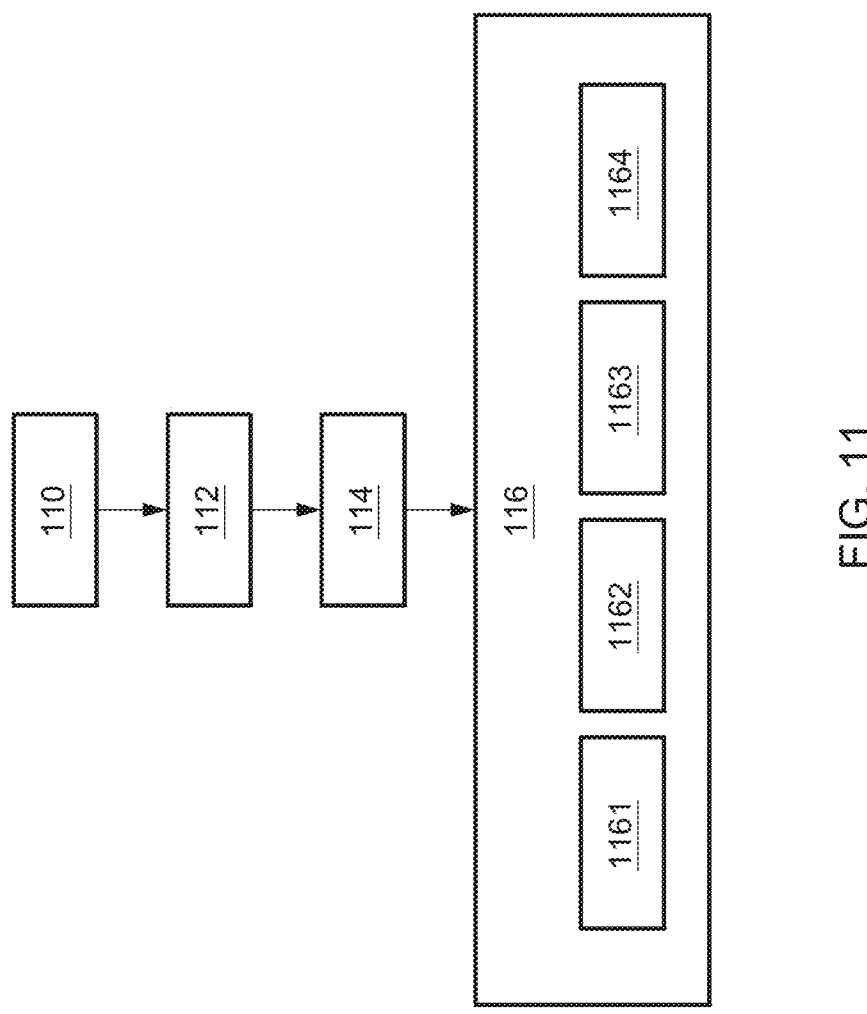
FIG. 11 illustrates a flow chart including operations for manufacturing a semiconductor device, in accordance with some embodiments of the present disclosure.

FIG. 11 illustrates a flow chart including operations for manufacturing a semiconductor device, in accordance with some embodiments of the present disclosure. In operation 110, a first semiconductor component may be formed. The first semiconductor component may include a first transistor and a second transistor. In operation 112, a bonding layer may be formed on the first semiconductor component. In operation 114, a second semiconductor component may be formed on the bonding layer.

In some embodiments, the operation 116 may include four operations 1161, 1162, 1163 and 1164. In operation 116, an acoustic transducer mat be formed and embedded within the second semiconductor component. In operation 1161, a space gap of the acoustic transducer may be formed. In operation 1162, a membrane of the acoustic transducer may be formed adjacent to a top surface of the space gap. The membrane may include piezoelectric material or dielectric material. In operation 1163, a top electrode may be formed above the membrane. In operation 1164, a bottom electrode may be formed above the membrane.

While disclosed methods (e.g., operations 110 to 1164) are illustrated and described below as a series of acts or events, it will be appreciated that the illustrated ordering of such acts or events are not to be interpreted in a limiting sense. For example, some operations may occur in different orders and/or concurrently with other acts or events apart from those illustrated and/or described herein. In addition, not all illustrated acts may be required to implement one or more aspects or embodiments of the description herein. Further, one or more of the acts depicted herein may be carried out in one or more separate acts and/or phases.

Some embodiments of the present disclosure provide a semiconductor device. The semiconductor device includes a first semiconductor component, a bonding layer and a second semiconductor component. The first semiconductor component includes a first transistor formed on a substrate and a second transistor formed on the substrate and separated from the first transistor. The bonding layer is provided on the first semiconductor component. The second semiconductor component is provided on the bonding layer and includes an acoustic transducer. The acoustic transducer is controlled by the first transistor and the second transistor to execute a photoacoustic sensing. The acoustic transducer comprises a space gap and a least a portion of the space gap is surrounded by the bonding layer.

Some embodiments of the present disclosure provide a semiconductor system. The semiconductor system includes a plurality of semiconductor devices. Each semiconductor device includes an acoustic transducer and a set of transistor. The acoustic transducer includes a capacitive micro-machined ultrasonic transducer or a piezoelectric micro-machined ultrasonic transducer. The transistors are configured to drive the acoustic transducer. Each of the semiconductor devices is spaced apart from another by a predetermined distance, and the predetermined distance is smaller than a sound wavelength of the acoustic transducer.

Some embodiments of the present disclosure provide a method for manufacturing a semiconductor device. The method includes forming a first semiconductor component, wherein the first semiconductor component comprises a first transistor and a second transistor; forming a bonding layer on the first semiconductor component; forming a second semiconductor component on the bonding layer; and forming an acoustic transducer embedded within the second semiconductor component, wherein the first transistor and the second transistor are configured to control the acoustic transducer.

The foregoing outlines structures of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A semiconductor device, comprising:
    a first semiconductor component, comprising:
        a substrate;
        a first transistor, formed on the substrate;
        a second transistor, formed on the substrate and separated from the first transistor;
        a first insulating layer formed on the substrate and a second insulating layer formed on the first insulating layer, wherein a plurality of first metal structures embedded within the second insulating layer, and a drain structure and a source structure of the first transistor are electrically connected to a portion of the first metal structures;
    a bonding layer, provided on the first semiconductor component; and
    a second semiconductor component, provided on the bonding layer, comprising:
        an acoustic transducer, controlled by the first transistor and the second transistor to execute a photoacoustic sensing, wherein the acoustic transducer comprises a space gap, and a least a portion of the space gap is surrounded by the bonding layer.

2. The semiconductor device of claim 1, wherein the acoustic transducer further comprises:
    a membrane, formed adjacent to a top surface of the space gap;
    a first electrode, contacting a top surface of the membrane; and
    a second electrode, wherein the membrane is formed between the first electrode and the second electrode.

3. The semiconductor device of claim 2, wherein the membrane comprises a dielectric material, and the membrane is physically separated from the second electrode.

4. The semiconductor device of claim 2, wherein the membrane comprises piezoelectric material, and the membrane is in direct contact with the second electrode.

5. The semiconductor device of claim 2, wherein the membrane comprises a shape of circle, oval, triangle, rectangle or hexagon.

6. The semiconductor device of claim 1, wherein gate structures of the first transistor and the second transistor are formed within the first insulation layer.

7. The semiconductor device of claim 6, wherein the drain structure and the source structure of the first transistor are electrically connected to the portion of the first metal structures through a connecting structure; and
    wherein the first semiconductor component further comprises:
        a plurality of second metal structures, formed above and separated from the first metal structures, wherein the second metal structures are embedded within the second insulating layer.

8. The semiconductor device of claim 7, wherein the first transistor is NMOS transistor, and the second transistor is PMOS transistor.

9. The semiconductor device of claim 7, wherein the second semiconductor component comprises:

a passivation layer, provided on the bonding layer; and a via structure, penetrating the passivation layer, wherein a bottom portion of the via structure contacts at least one of the second metal structures, and a first area of the via structure is uncovered by the passivation layer.

10. The semiconductor device of claim 9, further comprising:

a matching material, formed on the passivation layer, wherein an impedance of the matching material is smaller than that of the second insulating layer.

11. A semiconductor system, comprising:

a plurality of semiconductor devices, each comprising:

an acoustic transducer, comprising a capacitive micromachined ultrasonic transducer (CMUT) or a piezoelectric micromachined ultrasonic transducer (PMUT);

a set of transistors on a substrate, configured to drive the acoustic transducer;

a first insulating layer formed on the substrate and a second insulating layer formed on the first insulating layer, wherein a drain structure and a source structure of one of the set of transistors are coupled to a metal structure embedded in the second insulating layer:

wherein each of the semiconductor devices is spaced apart from another by a distance, and the distance is smaller than a sound wavelength of the acoustic transducer.

12. The semiconductor system of claim 11, wherein the semiconductor devices are distributed in a figure of triangle, diamond, square or rectangle.

13. The semiconductor system of claim 11, wherein the semiconductor devices comprise:

a plurality of first semiconductor devices, each comprising the CMUT; and a plurality of second semiconductor devices, each comprising the PMUT.

14. The semiconductor system of claim 13, wherein the first semiconductor devices and the second semiconductor devices are interleaved or lined in order.

15. The semiconductor system of claim 13, wherein the first semiconductor devices are surrounded by the second semiconductor devices, or the second semiconductor devices are surrounded by the first semiconductor devices.

16. The semiconductor system of claim 11, wherein the semiconductor system comprises:

a plurality of light emitting devices, encircling the semiconductor devices.

17. The semiconductor system of claim 16, wherein the light emitting devices comprise visible light micro-LEDs, ultraviolet micro-LEDs, or near infrared micro-LEDs.

18. The semiconductor system of claim 17, wherein the semiconductor devices are surrounded by the near infrared micro-LEDs, the near infrared micro-LEDs are surrounded by the visible light micro-LEDs, and the visible light micro-LEDs are surrounded by the ultraviolet micro-LEDs.

19. A semiconductor system, comprising:

a plurality of semiconductor devices, each comprising an acoustic transducer and transistors that are configured to drive the acoustic transducer, wherein the semiconductor devices are separated from each other by a distance, and the distance is smaller than a sound wavelength of the acoustic transducer, and a first insulating layer and a second insulating layer are sequentially formed on the substrate, wherein a drain structure and a source structure of one of the transistors are coupled to a metal structure embedded in the second insulating layer; and a plurality of light emitting devices surrounding a region where the semiconductor devices are arranged.

20. The semiconductor system of claim 19, wherein the plurality of semiconductor devices comprise at least one capacitive micromachined ultrasonic transducer (CMUT) and at least one piezoelectric micromachined ultrasonic transducer (PMUT).

*    *    *    *    *